US008481489B2

(12) United States Patent
Abribat et al.

(10) Patent No.: US 8,481,489 B2
(45) Date of Patent: Jul. 9, 2013

(54) GH SECRETAGOGUES AND USES THEREOF

(75) Inventors: Thierry Abribat, St-Foy-les-Lyon (FR); Andre De Villers, Outremont (CA); Alcide Chapdelaine, Ile des Soeurs (CA); Soraya Allas, Iles des Soeurs (CA); Denis Gravel, Saint-Lambert (CA)

(73) Assignee: Theratechnologies Inc., Montreal (CA)

( * ) Notice: Subject to any disclaimer, the term of this patent is extended or adjusted under 35 U.S.C. 154(b) by 598 days.

(21) Appl. No.: 12/239,697

(22) Filed: Sep. 26, 2008

(65) Prior Publication Data
US 2009/0253623 A1 Oct. 8, 2009

Related U.S. Application Data

(60) Division of application No. 11/877,395, filed on Oct. 23, 2007, now abandoned, which is a continuation of application No. 10/969,463, filed on Oct. 20, 2004, now Pat. No. 7,316,997, which is a continuation-in-part of application No. PCT/CA03/00827, filed on May 29, 2003.

(51) Int. Cl.
*A61K 38/25* (2006.01)
(52) U.S. Cl.
USPC ........................................ 514/11.2
(58) Field of Classification Search
None
See application file for complete search history.

(56) References Cited

U.S. PATENT DOCUMENTS

| 5,861,379 | A | 1/1999 | Ibea et al. |
| 5,939,386 | A | 8/1999 | Ibea et al. |
| 6,020,311 | A | 2/2000 | Brazeau et al. |
| 6,194,384 | B1 * | 2/2001 | Brazeau et al. ............... 514/12 |
| 6,696,063 | B1 | 2/2004 | Torres |
| 2005/0197288 | A1 | 9/2005 | Abribat et al. |

FOREIGN PATENT DOCUMENTS

| CA | 2367461 | 9/2000 |
| WO | WO-9709060 | 3/1997 |
| WO | WO 0013650 | 3/2000 |
| WO | WO-0014236 | 3/2000 |
| WO | WO-2005037307 | 4/2005 |

OTHER PUBLICATIONS

Dubreuil & Brazeau "Increased insulin-like growth factor-1 concentrations following injection or implantation of a human growth hormone-releasing factor (GRF) analog in growing pigs." Journal of Animal Science, (1999) vol. 77, No. Suppl. 1, pp. 161. print. Meeting Info.: Meeting of the American Society of Animal Science. Indianapolis, Indiana, USA.*
Theratechnologies Inc. "Theratechnologies announces positive results of phase II trial of ThGRF" DrugWeek: News RX, Aug. 2, 2002.*
Theratechnoligies Inc. "Theratechnologies announces positive results of an efficacy and safety phase II clinical trial of ThGRF in sleep maintenance insomnia," www.theratech.com, May 29, 2002.*
Theratechnologies Inc. "Theratechnologies and Saki Chemicals in landmark licensing agreement to develop and market ThGRF peptide in Japan," www.theratech.com, Feb. 5, 2002.*
Merriam et al. ("Growth Hormone Releasing Hormone Treatment in Normal Aging," Journal of Anti-Aging Medicine, 2001, vol. 4, 331-343).*
Hoffman ("Sleep in the Older Adult: Implications for Nurses (CE)", Geriatric Nursing, 2003, 24, 210-216).*
Prinz ("Age impairments in sleep, metabolic and immune functions," Experimental Gerontology, 2004, 39, 1739-1743).*
Theratechnologies Inc. 2004. Theratechnologies Presents Results from its HIV-Associated Lipodystrophy Phase II Study on THGRF at the 12th International Congress of Endocrinology. online: www.theratech.com/en/news-events/news.
Khorram, O., et al. 1997. Effects of [Norleucine 27] Growth Hormone-Releasing Hormone (GHRH) (1-29)-NH2 Administration on the Immune System of Aging Men and Women. Journal of Clinical Endocrinology and Metabolism 82(11): 3590-3596.
Nagaya, N., et al. 2005. Treatment of Cachexia with Ghrelin in Patients with COPD. Chest 128(3): 1187-1193.
Koutkia, P., et al. 2005. Effects of Growth Hormone-Releasing Hormone on Bone Turnover in Human Immunodeficiency Virus-Infected Men with Fat Accumulation. The Journal of Clinical Endocrinology and Metabolism 90(4): 2154-2160.
Falutz, J., et al. 2005. A Placebo-Controlled, Dose-Ranging Study of a Growth Hormone Releasing Factor in HIV-Infected Patients with Abdominal Fat Accumulation. AIDS 19: 1279-1287.
"Wasting syndrome treatment advocacy issues" http://www.medibolics.com/NewLipodystrophyDrug.htm, May 22, 2003.
Garcia-Viejo et al. Strategies for treating HIV-related lipodystrophy, Expert Opin., 2001, 10, 1443-56.
Theratechnologies Inc., Press Release dated May 22, 2003; accessed at http://www.theratech.com/en/ news-events/news.php?id=74.
Nagaya et al., 2005. Treatment of Cachexia with Ghrelin in Patients with COPD. *Chest* 128(3): 1187-1193.
Falutz et al., 2005. A Placibo-Controlled, Dose-Ranging Study of a Growth Hormone Releasing Factor in HIV-infected Patients with Abdominal Fat Accumulation. *AIDS* 19:1279-1287.
Koutkia et al., 2005. Effects of Growth Hormone-Releasing Hormone on Bone Turnover in Human Immunodeficiency Virus—infected Men with Fat Accumulation. *The Journal of Clinical Endocrinology and Metabolism* 90(4): 2154-2160.
Khorram et al., 1997. Effects of [Norleucine 27] Growth-Hormone-Releasing Hormone (GHRH) (1-29)-NH2 Administration on the Immune System of Aging Men and Women. *Journal of Clinical Endocrinology and Metabolism* 82(11):3590-3596.

(Continued)

Primary Examiner — Christina Bradley
(74) Attorney, Agent, or Firm — Fish & Richardson P.C.

(57) ABSTRACT

The invention relates to use of a GH secretagogue (e.g. GRF or an analog thereof) for (1) altering a lipid parameter in a subject; (2) altering a body composition parameter in a subject, (3) treating a condition characterized by deficient or decreased bone formation in a subject (4) improving daytime vigilance and/or cognitive function in a subject, (5) improving a metabolic condition in a subject, (6) improving anabolism in a catabolic condition in a subject, and/or (7) improving and/or reconstituting immune function in a subject.

7 Claims, 7 Drawing Sheets

OTHER PUBLICATIONS

Engelson et al., Effect of Recombinant Human Growth Hormone in the Treatment of Visceral Fat Accumulation in HIV Infection, *Journal of Acquired Immune Deficiency Syndromes*, 2002, vol. 30, pp. 379-391.

Kotler et al., Effects of Growth Hormone on Abnormal Visceral Adipose Tissue Accumulation and Dyslipidemia in HIV-infected Patients, *J. Acquir. Immune Defic. Syndr.*, Mar. 1, 2004, vol. 35, No. 3, pp. 239-252.

Rietschel, Petra, et al., "Assessment of Growth Hormone Dynamics in Human Immunodeficiency Virus-Related Lipodystrophy", The Journal of Clinical Endocrinology and Metabolism, 2001, vol. 86, No. 2, pp. 504-510.

Miller et al., Visceral abdominal-fat accumulation associated with use of indinavir, *The Lancet*, Mar. 21, 1998, vol. 351, pp. 871-875.

Wanke et al., Recombinant human growth hormone improves the fat redistribution syndrome (lipodystrophy) in patients with HIV, *AIDS*, 1999, vol. 13, No. 15. pp. 2099-2103.

Lo et al., The Effects of Recombinant Human Growth Hormone on Body Composition and Glucose Metabolism in HIV-Infected Patients with Fat Accumulation, *The Journal of Clinical Endrocrinology & Metabolism*, 2001, vol. 86, No. 8, pp. 3480-3487.

Koutkia et al., Growth Hormone-Releasing Hormone in HIV-Infected Men with Lipodystrophy, *JAMA*, Jul. 14, 2004, vol. 292, No. 2, pp. 210-218.

Abribat et al., TH9507 A New Growth Hormone-Releasing Factor (GRF) Analogue is a Powerful Insulin-Like Growth Factor-1 (IGF-1) Inducer in 50-60 Years Old Healthy Subjects: A 7-Day, Randomized Multidose Study, The Endocrine Society's 84th Annual Meeting, 2001, Denver, p. P2-292.

Clemmons et al., Safety Assessment and Metabolic Effects of TH9507, a Growth Hormone-Releasing Factor Analogue (GRF), in Patients with Type 2 Diabetes Mellitus, The Endocrine Society's 86th Annual Meeting, 2003, Philadelphia, p. P2-354.

Park et al., Are dual-energy X-ray absorptiometry regional estimates associated with visceral adipose tissue mass? *International Journal of Obesity*, 2002, vol. 26, pp. 978-983.

Hadigan et al., Metabolic Effects of Rosiglitazone in HIV Lipodystrophy, *Annals of Internal Medicine*, May 2004, vol. 140, No. 10, pp. 786-794.

Hadigan et al., Metformin in the Treatment of HIV Lipodystrophy Syndrome: A Randomiszed Controlled Trial, *JAMA*, Jul. 26, 2000, vol. 284, No. 4, pp. 472-477.

Johannsson et al., Growth Hormone Treatment of Abdominally Obese Men Reduces Abdominal Fat Mass, Improves Glucose and Lipoprotein Metabolism, and Reduces Diastolic Blood Pressure, *Journal of Clinical Endocrinology and Metabolism*, 1997, vol. 82, No. 3, pp. 727-734.

Calao et al., Improved Cardiovascular Risk Factors and Cardiac Performance after 12 Months of Growth Hormone (GH) Replacement in Young Adult Patients with GH Deficiency, *The Journal of Clinical Endocrinology & Metabolism*, 2001, vol. 86, No. 5, pp. 1874-1881.

Thornton et al., Chronic [D-Ala^2] GHRH administration increases working memory in aged animals, *Abstracts of the Society for Neuroscience*, vol. 23, No. 1, 1997, p. 532.

Alvarez et al., Effects of GRF (1-29) NH2 on Short-Term Memory: Neuroendocrine and Neuropsychological Assessment in healthy Young Subjects, *Meth. Find. Exp. Clin. Pharmacol.*, 1990, vol. 12, No. 7, pp. 493-499.

Schneider-Rivas et al., Modulation of Long-Term Memory and Extinction Responses Induced by Growth Hormone (GH) and Growth Hormone Releasing Hormone (GHRH) in Rats, *Life Sciences*, vol. 56, No. 22, 1995, pp. 433-441.

Aleman et al., Insulin-Like Growth Factor-1 and Cognitive Function in Healthy Older Men, *Journal of Clinical Endocrinology and Metabolism*, vol. 84, No. 2, 1999, pp. 471-475.

Theratechnologies Inc., ThGRF in HIV-related lipodystrophy: Phase II clinical trial in Canada and the US, May 22, 2003, http://www.medibolics.com/New LipodystrophyDrug.htm.

Theratechnologies Press Releases, Theratechnologies clinically demonstrates improvement in immune function among elderly with ThGRF peptide, Jun. 6, 2002, pp. 1-3, http://www.theratech.com/english/press/2002/0606-2002.htm.

Carr et al., A syndrome of peripheral lipodystrophy, hyperlipidaemia and insulin resistance in patients receiving HIV protease inhibitor, *AIDS*, 1998, vol. 12, pp. F51-F58.

Hadigan et al., Metabolic Abnormalities and Cardiovascular Disease Risk Factors in Adults with Human Immunodeficiency Virus Infection and Lipodystrophy, *Clin. Infect. Dis.*, 2001, vol. 32, No. 1, pp. 130-139.

Friis-Moller et al., Combinatino Antiretroviral Therapy and the Risk of Myocardial Infraction, *The New England Journal of Medicine*, Nov. 2003, vol. 349, No. 21, pp. 1993-2003.

Pouliot et al., Visceral Obesity in Men: Associations with Glucose Tolerance, Plasma Insulin, and Lipoprotein Levels, Diabetes, vol. 41, Jul. 1992, pp. 826-834.

Meininger et al., Body-composition measurements as predictors of glucose and insulin abnormalities in HIV-positive men^ 1-3, *Am. J. Clin. Nutr.*, 2002, vol. 76, pp. 460-465.

Koutkla, Polyxeni, et al., "Metabolic regulation of growth hormone by free fatty acids, somatostatin, and ghrelin in HIV-lipodrystrophy", Am. J. Physiol. Endocrinol. Metab., 2004.

Chen, et al., Lipodystrophy in Human Immunodeficiency Virus-Infected Patients, The Journal of Clinical Endocrinology & Metabolism, 87(11):4845-4856, (2002).

Kato, et al., Regulation of Human Growth Hormone Secretion and Its Disorders, Internal Medicine, vol. 41, No. 1, pp. 7-12, (Jan. 2002).

Koutkia, et al., Metabolic regulation of growth hormone by free fatty acids, somatostatin, and ghrelin in HIV-lipodystrophy, Am J Physiol Endocrinol Metab, 286:E296-E303, (Publication date Oct. 14, 2003).

Meininger, et al., Elevated Concentrations of Free Fatty Acids Are Associated With Increased Insulin Response to Standard Glucose Challenge in Human Immunodeficiency Virus-Infected Subjects With Fat Redistribution, Metabolism, vol. 51, No. 2, pp. 260-266, (Feb. 2002).

Mulroney, et al., HIV gp120 inhibits the somatotropic axis: A possible GH-releasing hormone receptor mechanism for the pathogenesis of AIDS wasting, Proc. Natl. Acad. Sci. USA, vol. 95, pp. 1927-1932, (Feb. 1998).

Rietschel, et al., Assessment of Growth Hormone Dynamics in Human Immunodeficiency Virus-Related Lipodystrophy, The Journal of Clinical Endocrinology & Metabolism, vol. 86, No. 2, pp. 504-510, (2001).

Schauster, et al., Diabetes Mellitus Associated with Recombinant Human Growth Hormone for HIV Wasting Syndrome, Pharmacotherapy vol. 20, pp. 1129-1134, (Nov. 2000).

Cuneo et al., The Australian Multicenter Trial of Growth Hormone (GH) Treatment in GH-Deficient Adults, J. Clin. Endocrinol Metab., 83:107-116 (1998).

Grunfeld et al., Recombinant Human Growth Hormone to Treat HIV-Associated Adipose Redistribution Syndrome 12-Week Induction and 24-Week Maintenance Therapy, J. Acquir. Immune Defic. Syndr., 45(3):286-297 (2007).

Mauss et al., Reversal of Protease Inhibitor-Related Visceral Abdominal Fat Accumulation with Recombinant Human Growth Hormone, Annals of Internal Medicine, 131(4):313-314 (1999).

Merriam-Webster, 2011, Predominant—Definition and More from the Free Meriam-Webster Dictionary website.

Torres et al., Recombinant human growth hormone improves truncal adiposity and 'buffalo humps' in HIV-positive patients on HAART, AIDS 13:2479-2481 (1999).

Cordido et al., "The decreased growth hormone response to growth hormone releasing hormone in obesity is associated to cardiometabolic risk factors," Mediators Inflamm., vol. 2010, Article ID 434562, 8 pages, Submitted Sep. 24, 2009; Accepted Nov. 4, 2009.

"Peptide may help with frat accumulation," AIDS Patient Care and STDs, (Sep. 2003), vol. 17, No. 9, p. 489.

Ferdinandi et al., "TH9507: embryofetal and fertiity studies of a growth hormone-releasing factor (GRF) analogue," 42nd Annual Meeting of the Society of Toxicology, Salt Lake City, UT, Mar. 9, 2003).

Abribat et al., "TH9507, a growth hormone-releasing factor analogue (GRF), does not impair overall glucose control and decreases non-HDL cholesterol in patients with Type 2 diabetes." Diabetes & Metabolism, (Aug. 2003), vol. 29; Series 2, p. 4S129, Abstract 1796. Meeting Info: 18th International Diabetes Federation Congress. Paris, France, Aug. 2003.

Washer et al., "TH9507: safety studies of a growth-hormone releasing factor (GFR) analogue," 42nd Annual Meeting of the Society of Toxicology, Salt Lake City, UT, Mar. 9, 2003.

Thornton et al., "Chronic [D-Ala2]-Growth Hormonoe-Releasing Hormone Administration Attenuates Age-Related Deficits in Spatial Memory", Journal of Gerontology: Biological Sciences; vol. 55A; No. 1; pp. B106-B112 (2000).

Deijen, J.B., et al., "Cognitive Changes During Growth Hormone Replacement in Adult Men", Psychoneuroendocrinology, vol. 23. No. I , pp. 45-55, 1998.

Extended European Search Report re Application11168850.3-1521 2382984, dated Oct. 26, 2011.

Schneider-Rivas, Sonia et al., "Modulation of Long-Term Memory and Extinction Responses Induced by Growth Hormone (GH) and Growth Hormone Releasing Hormone (GHRH) in Rats", Life Sciences, vol. 56, No. 22, pp. 433-441, 1995.

Van Dam, P.S., et al., "Growth hormone, insulin-like growth factor I and cognitive function in adults", Growth Hormone & IGF Research, Supplement B, pp. 69-73, 2000.

\* cited by examiner

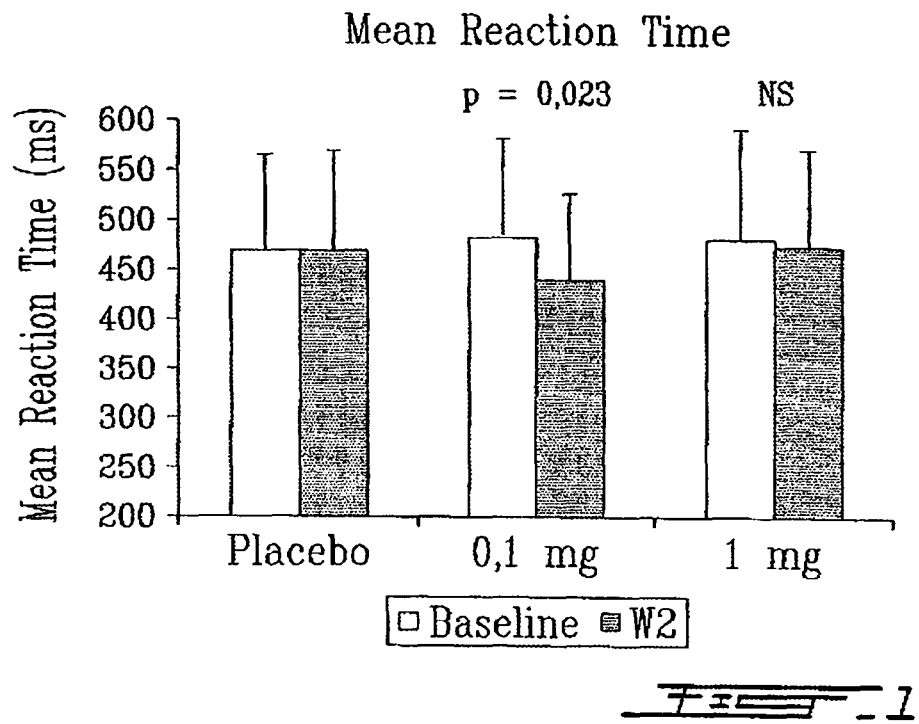
FIG_1
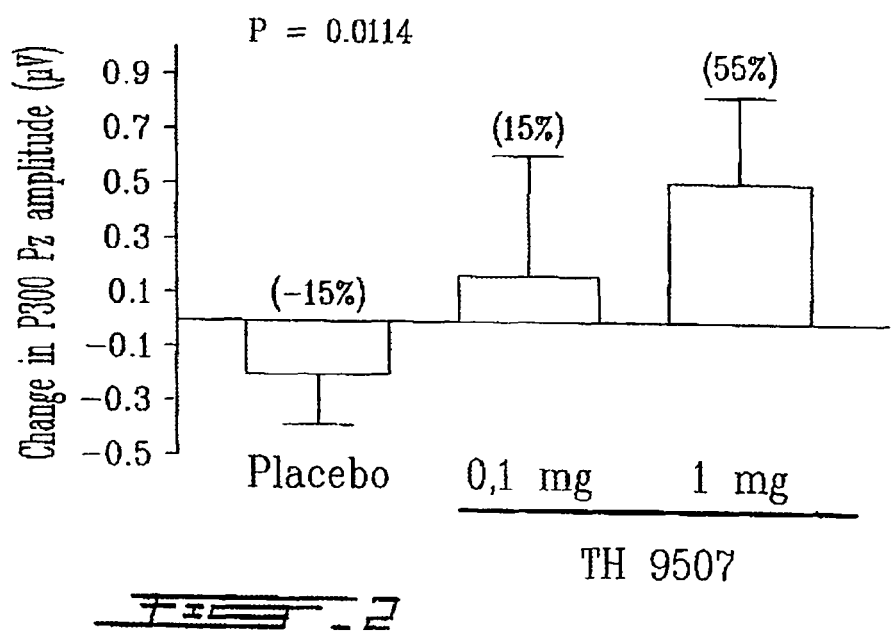
FIG_2

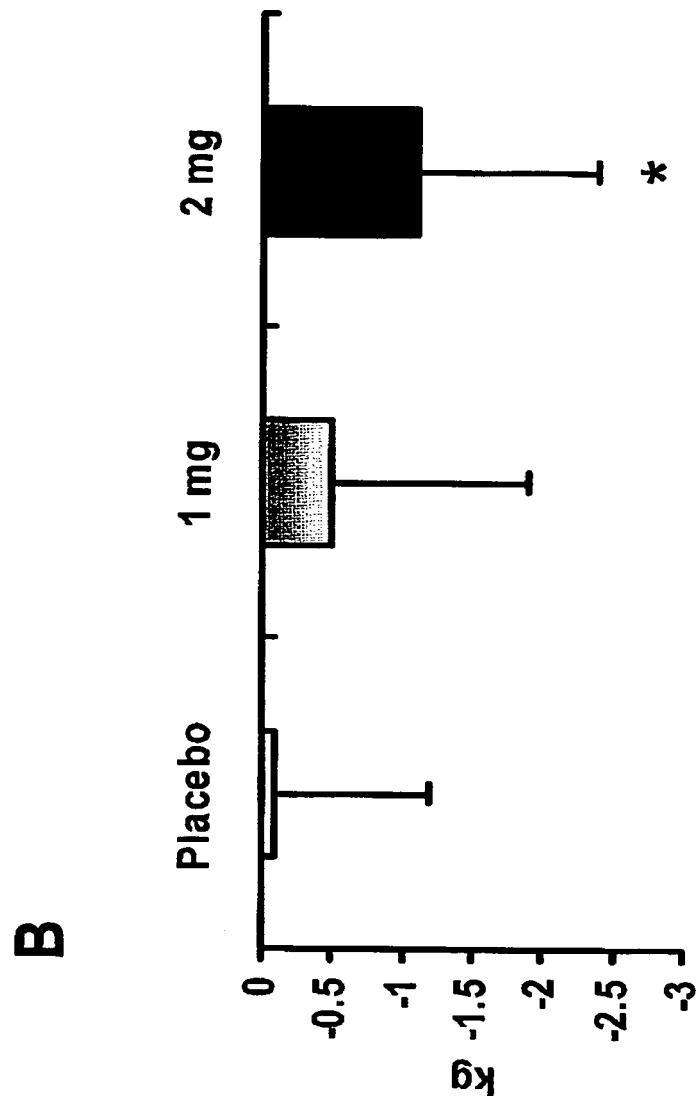
Figure 7: continued

GH SECRETAGOGUES AND USES THEREOF

CROSS-REFERENCE TO RELATED APPLICATION

This application is a divisional of prior application Ser. No. 11/877,395, filed Oct. 23, 2007, which is a continuation of prior application Ser. No. 10/969,463, filed Oct. 20, 2004, now U.S. Pat. No. 7,316,997, which is a continuation in part of PCT International Patent Application No. PCT/CA03/00827 filed May 29, 2003. The aforementioned applications are hereby incorporated herein by reference in their entireties.

FIELD OF THE INVENTION

The invention relates to growth hormone (GH) secretagogues, such as GH releasing factor (GRF) and analogs thereof, and uses thereof.

BACKGROUND OF THE INVENTION

Syndromes Associated with Fat Accumulation

Physiological systems include a number of lipid compounds/molecules such as triglycerides and sterols (e.g. cholesterol), and associated carriers/complexes such as HDL, LDL, etc. Adverse levels or metabolism of such molecules is associated with related conditions such as fat accumulation, and associated disease.

Fat accumulation is observed in a range of conditions or syndromes such as obesity, metabolic syndrome, and the recently described HIV-related lipodystrophy syndrome. All these conditions include features which are known to increase the risk of diabetes and/or cardiovascular diseases.

The metabolic syndrome, also known as syndrome X, affect persons with frank obesity as well as those with an increased amount of abdominal fat, and is characterized by insulin resistance, dyslipidemia (hypertriglyceridemia, low serum HDL cholesterol levels, and increased LDL cholesterol levels) and hypertension.

HIV-infected patients treated with highly active antiretroviral therapy (HAART) commonly experience changes in fat distribution that include increased visceral and central fat accumulation (1), as well as loss of extremity and subcutaneous fat (especially in the facial fat pads, limbs and buttocks) in association with insulin resistance and dyslipidemia (2, 3). Recent data suggest increased cardiovascular disease and myocardial infarction rates in patients treated with prolonged antiretroviral therapy (ART) (4). In non HIV-infected patients (5) and among HIV-infected patients with changes in fat distribution (6), increased waist to hip ratio (WHR) and central fat accumulation is related to increased metabolic risk indices.

Growth Hormone is known for its lipolytic properties, and its potential role in reversing several of the body fat and associated metabolic abnormalities has been actively studied. Beneficial effects have been shown in GH-deficient individuals (Gotherstrom G. et al., *J Clin Endocrinol Metab* 2001 86(10):4657-4665) and non-HIV patients with abdominal obesity (Johannsson G, et al., *J Clin Endocrinol Metab* 1997, 82(3):727-734). Recent studies also suggest that that GH levels are reduced in HIV-infected patients, and correlate inversely with excess visceral fat accumulation (7, 8). Studies using higher dose, pharmacologic GH administration have resulted in reduced visceral adiposity in this population, but are associated with increased insulin resistance and side effects (9-12).

Cognitive Function

Cognitive abilities are impaired in a number of conditions including advancing age. Deleterious changes observed with aging affect particularly fluid intelligence, or abilities involving concept formation, rule discovery, planning behavior, and non-verbal reasoning. Conversely, crystallized intelligence, or abilities dependent upon accumulated experience and education is relatively resistant to age-related decline. It has been suggested that the decline in GH and IGF-1 observed with aging contribute to the impaired cognitive function.

Evidence exists from both animal and human studies that administration of GRF, GH or IGF-1 has significant effect on cognitive functions in conditions where these functions are impaired. For example, this has been demonstrated with GH therapy in GH-deficient adults (Deijen J B, et al., *Psychoneuroendocrinology* 1998 23(1):45-55), and with administration of IGF-1 or GRF in the healthy elderly (Aleman A et al., *J Clin Endocrinol Metab* 1999 84(2):471-475; Vitiello M. V., et al., *Gerontologist* 2002 40(Special Issue 1):39).

Immune Function

Aging is accompanied by diminished circulating GH and IGF-1 levels observed in parallel with a declined function of the immune system, particularly affecting the T-cell mediated immunity. The age-related T-cell immune deficiency has been partly attributed to a progressive atrophy of the thymus gland and is considered to be causally related to the increased risk and severity of acquired infections observed in the elderly.

GH and IGF-1 are known to play an integrating role in the development and function of the immune system, as endocrine and/or autocrine/paracrine factors, and their administration has been shown to reverse age-related immune changes. Immune enhancing effects of these factors have been investigated in other immune deficiency states and encouraging results have been observed in HIV-positive patients (Napolitano L A, et al., *AIDS* 2002 16(8):1103-1111) and in animal models of radiotherapy preceding bone marrow transplantation (Sun R, et al., *BMT Meetings*, February 22-26 Orlando, Fla., Abstract 27 2002:68-69).

Catabolism or Muscle Wasting

Muscle protein catabolism, or muscle wasting, accompanies many diseases including all critical illness, regardless of the primary cause of disease. It is an important factor for the long-term prognosis and the length of hospital stay and recovery, and may also be a limiting factor for survival. Although many therapeutic tools have been investigated including specific nutritional treatment, there is still a strong need for more effective strategies to counteract protein catabolism.

Previous studies have reported that GH treatment increases muscle mass in older patients. The anabolic effects or abilities of GH to reverse or attenuate muscle wasting have been investigated in several patient groups. GH has been shown to improve nitrogen balance, an index of net whole-body protein balance, after major gastro-intestinal surgery, burn injury, or major trauma. Anabolic effects have been translated into clinical benefits in COPD patients (improvement of the maximal inspiratory pressure) (Papte G S, et al., *Chest* 1991 99(6):1495-1500) and elderly patient undergoing surgery following hip fracture (improvement of functional recovery defined as return to independence) (Van der Lely A J, et al., *Eur J Endocrinol* 2000 143(5):585-592). Finally, rGH has been recently approved for management of AIDS-wasting based on results showing increased body weight, lean body mass and functional performance following 12 weeks of treatment (Schambelan M, et al., *Ann Intern Med* 1996 125(11):873-882).

However, the use of GH to treat conditions such as those noted above, has been associated with adverse side effects in some cases.

SUMMARY OF THE INVENTION

The invention relates to GH secretagogues (e.g. GRF and analogs thereof) and uses thereof.

Therefore, in a first aspect, the invention provides a method of altering a lipid parameter in a subject, said method comprising administering to said subject an agent selected from the group consisting of: (a) a growth hormone (GH) secretagogue; and (b) a composition comprising a GH secretagogue and a pharmaceutically acceptable carrier.

In a further aspect, the invention provides a package comprising an agent selected from the group consisting of (a) a growth hormone (GH) secretagogue; and (b) a composition comprising a GH secretagogue and a pharmaceutically acceptable carrier; together with instructions for altering a lipid parameter in a subject.

In a further aspect, the invention provides a use of an agent selected from the group consisting of: (a) a growth hormone (GH) secretagogue; and (b) a composition comprising a GH secretagogue and a pharmaceutically acceptable carrier; for altering a lipid parameter in a subject.

In a further aspect, the invention provides a use of a growth hormone (GH) secretagogue for the preparation of a medicament for altering a lipid parameter in a subject.

In a further aspect, the invention provides a method of altering a first body composition parameter of a subject, the method comprising administering to said subject an agent selected from the group consisting of (a) a growth hormone (GH) secretagogue; and (b) a composition comprising a GH secretagogue and a pharmaceutically acceptable carrier.

In a further aspect, the invention provides a package comprising an agent selected from the group consisting of: (a) a growth hormone (GH) secretagogue; and (b) a composition comprising a GH secretagogue and a pharmaceutically acceptable carrier; together with instructions for altering a first body composition parameter of a subject.

In a further aspect, the invention provides a use of an agent selected from the group consisting of: (a) a growth hormone (GH) secretagogue; and (b) a composition comprising a GH secretagogue and a pharmaceutically acceptable carrier; for altering a first body composition-parameter of a subject.

In a further aspect, the invention provides a use of a growth hormone (GH) secretagogue for the preparation of a medicament for altering a first body composition parameter of a subject.

In a further aspect, the invention provides a method of treating a condition characterized by deficient or decreased bone formation in a subject, said method comprising administering to said subject an agent selected from the group consisting of: (a) a growth hormone (GH) secretagogue; and (b) a composition comprising a GH secretagogue and a pharmaceutically acceptable carrier.

In a further aspect, the invention provides a package comprising an agent selected from the group consisting of: (a) a growth hormone (GH) secretagogue; and (b) a composition comprising a GH secretagogue and a pharmaceutically acceptable carrier; together with instructions for treating a condition characterized by deficient or decreased bone formation in a subject.

In a further aspect, the invention provides a use of an agent selected from the group consisting of: (a) a growth hormone (GH) secretagogue; and (b) a composition comprising a GH secretagogue and a pharmaceutically acceptable carrier; for treating a condition characterized by deficient or decreased bone formation in a subject.

In a further aspect, the invention provides a use of a growth hormone (GH) secretagogue for the preparation of a medicament for treating a condition characterized by deficient or decreased bone formation in a subject.

In further aspects, the invention relates to a method for (1) stimulating day-time vigilance and/or cognitive functions e.g. in conditions related to aging or mild cognitive impairment, (2) improving metabolic conditions associated with fat accumulation and/or hypercholesterolemia, (e.g. metabolic conditions including obesity, HIV-related lipodystrophy, metabolic syndrome or syndrome X), (3) improving anabolism in catabolic/wasting conditions (such as those observed in Chronic Renal Failure, congestive heart failure AIDS, following hip fracture, trauma, or major surgery, particularly in elderly subjects), and/or (4) improving immune function or reconstitution of immunodeficient states such as that associated aging, HIV or following high-dose chemotherapy and/or radiotherapy; the method comprising administering a GH secretagogue (e.g. GRF and analogs thereof) or a composition comprising a GH secretagogue and a pharmaceutically acceptable carrier; to a subject.

In further aspects, the invention relates to uses of a GH secretagogue (e.g. GRF and analogs thereof) or a composition comprising a GH secretagogue and a pharmaceutically acceptable carrier, for (1) stimulating day-time vigilance and/or cognitive functions e.g. in conditions related to aging or mild cognitive impairment, (2) improving metabolic conditions associated with fat accumulation and/or hypercholesterolemia, (e.g. metabolic conditions including obesity, HIV-related lipodystrophy, metabolic syndrome or syndrome X), (3) improving anabolism in catabolic/wasting conditions (such as those observed in Chronic Renal Failure, congestive heart failure AIDS, following hip fracture, trauma, or major surgery, particularly in elderly subjects), and/or (4) improving immune function or reconstitution of immunodeficient states such as that associated aging, HIV or following high-dose chemotherapy and/or radiotherapy.

In further aspects, the invention similarly relates to a package comprising an agent selected from the group consisting of: (a) a growth hormone (GH) secretagogue; and (b) a composition comprising a GH secretagogue and a pharmaceutically acceptable carrier; together with instructions for (1) stimulating day-time vigilance and/or cognitive functions (2) improving metabolic conditions associated with fat accumulation and/or hypercholesterolemia, (3) improving anabolism in catabolic/wasting conditions, and/or (4) improving immune function or reconstitution of immunodeficient states.

In further aspects, the invention similarly relates to a use of a GH secretagogue for the preparation of a medicament for (1) stimulating day-time vigilance and/or cognitive functions (2) improving metabolic conditions associated with fat accumulation and/or hypercholesterolemia, (3) improving anabolism in catabolic/wasting conditions, and/or (4) improving immune function or reconstitution of immunodeficient states.

In accordance with the present invention, there is provided a composition for (1) altering a lipid parameter in a subject; (2) altering a body composition parameter in a subject, (3) treating a condition characterized by deficient or decreased bone formation in a subject (4) improving daytime vigilance and/or cognitive function in a subject, (5) improving a metabolic condition in a subject, (6) improving anabolism in a catabolic condition in a subject, and/or (7) improving and/or reconstituting immune function in a subject, the composition comprising an effective amount of a GH secretagogue (e.g.

GRF compound or analog thereof) in association with a pharmaceutically acceptable carrier, excipient or diluent.

In embodiments, the metabolic condition is associated with fat accumulation and/or hypercholesterolemia, e.g. obesity, HIV-related lipodystrophy, metabolic syndrome and syndrome X.

In embodiments the catabolic condition is related to one selected from the group consisting of chronic renal failure, AIDS, hip fracture, trauma or major surgery in a subject.

BRIEF DESCRIPTION OF THE DRAWINGS

FIG. 1 illustrates the differences between treatment groups in changes from baseline to week 2 in the mean reaction time of the Continuous Performance Test (CPT);

FIG. 3 illustrates mean AUC of antigen-specific proliferative T cell response;

DETAILED DESCRIPTION OF THE INVENTION

Figure 2:
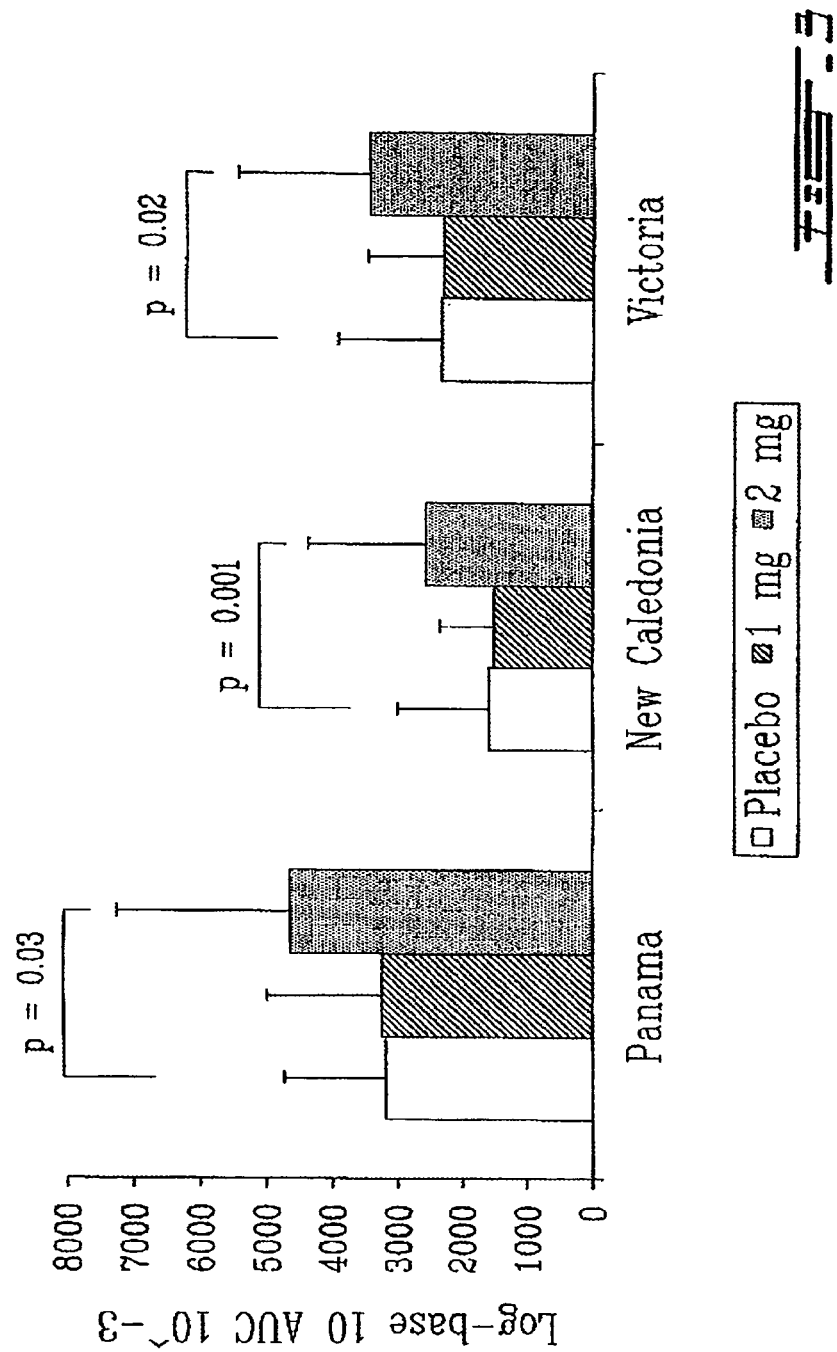
FIG. 2 illustrates changes from baseline to day 9 in Pz amplitude of evoked related potential (P300) during wakefulness.

In the studies described herein, the effect of (hexenoyl trans-3)hGRF(1-44)NH$_2$ (also referred to as TH9507 herein), a growth hormone releasing factor (GRF) analog, was assessed over 12 weeks in HIV-infected men and women with evidence of fat redistribution and increased truncal adiposity. The data herein demonstrate significant effects of TH9507 to increase lean body mass and reduce truncal fat and visceral fat and improve lipid parameters, sparing extremity and subcutaneous fat (Example 6). These effects were achieved with physiological increases in GH secretion and without adverse effects on blood glucose levels.

The studies described herein further demonstrate beneficial effects on bone markers.

The studies described herein further demonstrate a beneficial effect of Th9507 on daytime vigilance and cognitive function (Example 2), immune response (Example 3), wasting/catabolic conditions (Example 4) and non-HDL cholesterol (Example 5).

Accordingly, in a first aspect, the invention provides a method of altering a lipid parameter in a subject, said method comprising administering to said subject an agent selected from the group consisting of: (a) a growth hormone (GH) secretagogue; and (b) a composition comprising a GH secretagogue and a pharmaceutically acceptable carrier. In an embodiment, the method results in no or substantially no increase in blood glucose levels in said subject.

In a further aspect, the invention provides a package comprising an agent selected from the group consisting of (a) a growth hormone (GH) secretagogue; and (b) a composition comprising a GH secretagogue and a pharmaceutically acceptable carrier; together with instructions for altering a lipid parameter in a subject. In an embodiment, the above-mentioned alteration of a lipid parameter results in no or substantially no increase in blood glucose levels in said subject.

In a further aspect, the invention provides a use of an agent selected from the group consisting of (a) a growth hormone (GH) secretagogue; and (b) a composition comprising a GH secretagogue and a pharmaceutically acceptable carrier; for altering a lipid parameter in a subject. In an embodiment, the above-mentioned alteration of a lipid parameter results in no or substantially no increase in blood glucose levels in said subject.

In a further aspect, the invention provides a use of a growth hormone (GH) secretagogue for the preparation of a medicament for altering a lipid parameter in a subject. In an embodiment, the above-mentioned alteration of a lipid parameter results in no or substantially no increase in blood glucose levels in said subject.

In an embodiment, the above-noted the alteration of a lipid parameter is selected from the group consisting of: (a) a decrease in cholesterol; (b) a decrease in non-HDL cholesterol; (c) a decrease in triglyceride; (d) a decrease in the ratio of total cholesterol:HDL cholesterol; and (e) any combination of (a) to (d).

In an embodiment, the above-noted lipid parameter is associated with a condition selected from the group consisting of lipodystrophy, lipohypertrophy, obesity, dyslipidemia, hypertriglyceridemia and syndrome X.

In a further aspect, the invention provides a method of altering a first body composition parameter of a subject, the method comprising administering to said subject an agent selected from the group consisting of (a) a growth hormone (GH) secretagogue; and (b) a composition comprising a GH secretagogue and a pharmaceutically acceptable carrier. In an embodiment, the method results in no or substantially no decrease in a second body composition parameter of the subject, wherein the second body composition parameter is selected from the group consisting of: (i) limb fat; (ii) subcutaneous fat; (iii) subcutaneous abdominal tissue (SAT); and (iv) any combination of (i) to (iii).

In a further aspect, the invention provides a package comprising an agent selected from the group consisting of: (a) a growth hormone (GH) secretagogue; and (b) a composition comprising a GH secretagogue and a pharmaceutically acceptable carrier; together with instructions for altering a first body composition parameter of a subject. In an embodiment, the above-mentioned alteration of a first body composition parameter results in no or substantially no decrease in a second body composition parameter of the subject, wherein the second body composition parameter is selected from the group consisting of (i) limb fat; (ii) subcutaneous fat; (iii) subcutaneous abdominal tissue (SAT); and (iv) any combination of (i) to (iii).

In a further aspect, the invention provides a use of an agent selected from the group consisting of: (a) a growth hormone (GH) secretagogue; and (b) a composition comprising a GH secretagogue and a pharmaceutically acceptable carrier; for altering a first body composition parameter of a subject. In an embodiment, the above-mentioned alteration of a first body composition parameter results in no or substantially no decrease in a second body composition parameter of the subject, wherein the second body composition parameter is selected from the group consisting of (i) limb fat; (ii) subcutaneous fat; (iii) subcutaneous abdominal tissue (SAT); and (iv) any combination of (i) to (iii).

In a further aspect, the invention provides a use of a growth hormone (GH) secretagogue for the preparation of a medicament for altering a first body composition parameter of a subject. In an embodiment, the above-mentioned alteration of a first body composition parameter results in no or substantially no decrease in a second body composition parameter of the subject, wherein the second body composition parameter is selected from the group consisting of (i) limb fat; (ii) subcutaneous fat; (iii) subcutaneous abdominal tissue (SAT); and (iv) any combination of (i) to (iii).

In an embodiment, the above-mentioned alteration of a first body composition parameter is selected from the group consisting of: (a) an increase in lean body mass; (b) a decrease in trunk fat; (c) a decrease in visceral fat; (d) a decrease in abdominal girth; (e) a decrease in visceral abdominal tissue (VAT); (f) a decrease in VAT:SAT ratio; and (g) any combination of (a) to (f).

In an embodiment, the first body composition parameter is associated with a condition selected from the group consisting of lipodystrophy, lipohypertrophy, obesity, dyslipidemia, hypertriglyceridemia and syndrome X.

In an embodiment, the above-mentioned alteration of a first body composition parameter results in an improvement of quality of life of the subject.

In a further aspect, the invention provides a method of treating a condition characterized by deficient or decreased bone formation or for treating bone dysfunction or defect, in a subject, said method comprising administering to said subject an agent selected from the group consisting of: (a) a growth hormone (GH) secretagogue; and (b) a composition comprising a GH secretagogue and a pharmaceutically acceptable carrier.

In a further aspect, the invention provides a package comprising an agent selected from the group consisting of: (a) a growth hormone (GH) secretagogue; and (b) a composition comprising a GH secretagogue and a pharmaceutically acceptable carrier; together with instructions for treating a condition characterized by deficient or decreased bone formation in a subject.

In a further aspect, the invention provides a use of an agent selected from the group consisting of: (a) a growth hormone (GH) secretagogue; and (b) a composition comprising a GH secretagogue and a pharmaceutically acceptable carrier; for treating a condition characterized by deficient or decreased bone formation in a subject.

In a further aspect, the invention provides a use of a growth hormone (GH) secretagogue for the preparation of a medicament for treating a condition characterized by deficient or decreased bone formation in a subject.

In an embodiment, the above-noted condition characterized by deficient or decreased bone formation is selected from the group consisting of osteopenia and osteoporosis.

In further aspects, the invention relates to uses of a GH secretagogue (e.g. GRF and analogs thereof) or a composition comprising a GH secretagogue and a pharmaceutically acceptable carrier, for (1) stimulating day-time vigilance and/or cognitive functions e.g. in conditions related to aging or mild cognitive impairment, (2) improving metabolic conditions associated with fat accumulation and/or hypercholesterolemia, (e.g. metabolic conditions including obesity, HIV-related lipodystrophy, metabolic syndrome or syndrome X), (3) improving anabolism in catabolic/wasting conditions (such as those observed in Chronic Renal Failure, congestive heart failure AIDS, following hip fracture, trauma, or major surgery, particularly in elderly subjects), and/or (4) improving immune function or reconstitution of immunodeficient states such as that associated aging, HIV or following high-dose chemotherapy and/or radiotherapy.

In further aspects, the invention similarly relates to a package comprising an agent selected from the group consisting of: (a) a growth hormone (GH) secretagogue; and (b) a composition comprising a GH secretagogue and a pharmaceutically acceptable carrier; together with instructions for (1) stimulating day-time vigilance and/or cognitive functions (2) improving metabolic conditions associated with fat accumulation and/or hypercholesterolemia, (3) improving anabolism in catabolic/wasting conditions, and/or (4) improving immune function or reconstitution of immunodeficient states.

In further aspects, the invention similarly relates to a use of a GH secretagogue for the preparation of a medicament for (1) stimulating day-time vigilance and/or cognitive functions (2) improving metabolic conditions associated with fat accumulation and/or hypercholesterolemia, (3) improving anabolism in catabolic/wasting conditions, and/or (4) improving immune function or reconstitution of immunodeficient states.

In an embodiment, the above-mentioned lipodystrophy is HIV-related lipodystrophy.

In an embodiment, the above-mentioned subject is HIV positive.

In an embodiment, the above-mentioned subject is receiving antiviral therapy.

In an embodiment, the above-mentioned subject suffers from a condition selected from the group consisting of diabetes, glucose intolerance and insulin resistance.

In an embodiment the above-mentioned GH secretagogue is administered at a dose of about 0.0001 to about 4 mg, in a further embodiment, about 0.0001 to about 2 mg, in a further embodiment, about 1 mg to about 2 mg, in a further embodiment, about 1 mg and in a further embodiment, about 2 mg.

In an embodiment, the agent is administered by a route selected from the group consisting of intravenous, oral, transdermal, subcutaneous, mucosal, intramuscular, intranasal, intrapulmonary, parenteral, intrarectal and topical. In an embodiment, the agent is administered by a subcutaneous route.

In an embodiment, the subject is a mammal, in a further embodiment, a human.

For the purpose of the present invention the following terms are defined bellow.

The term "analog" is intended to mean a molecule of different structure but having a biological function similar to the structures of the GRF or to a biologically functional fragment thereof which may include peptidomimetics. Peptidomimetics may be conveniently prepared by direct chemical synthesis using methods well known in the art.

The term "subject" is intended to mean any mammal including, but not limited to, human, canine, feline, equine, caprine, bovine, porcine and ovine.

The term "cognitive function" is intended to mean functions including, but not limited to thinking, reasoning, memory and problem solving.

The term "catabolic/wasting conditions" is intended to mean condition including, but not limited to, frail bones, low muscular mass and muscle wasting.

In the present application, the compound identified as TH9507 is the [hexenoyl-trans-3-Tyr1]hGRF(1-44)NH$_2$.

In various aspects, the methods and corresponding uses and packages described herein comprise administering to a subject a growth hormone (GH) secretagogue. "GH secretagogue" as used herein refers to any compound or molecule, natural or synthetic, which may result in, either directly or indirectly, GH secretion and/or an increase in GH secretion.

In embodiments, the GH secretagogue is a growth hormone-releasing factor (GRF; also referred to as growth hormone releasing hormone [GHRH]) or GRF analog.

In an embodiment, the GRF is human GRF (hGRF).

Human growth hormone-releasing factor (hGRF) is a peptide of 44 amino acids with a C-terminal NH$_2$ modification, referred to herein as hGRF(1-44)NH$_2$, and has the following structure:

(SEQ ID NO: 2)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-Gln-Gln-Gly-Glu-Ser-Asn-Gln-

Glu-Arg-Gly-Ala-Arg-Ala-Arg-Leu-NH$_2$

Therefore, the amino acid sequence of the just-noted 44 amino acid form is as follows:

(SEQ ID NO: 3)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-Gln-Gln-Gly-Glu-Ser-Asn-Gln-

Glu-Arg-Gly-Ala-Arg-Ala-Arg-Leu

The minimum active core comprises the first 29 amino acids of the above sequence, which is referred to herein as hGRF(1-29)NH$_2$, and has the following structure:

(SEQ ID NO: 4)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-NH$_2$

Therefore, the amino acid sequence of the just-noted 29 amino acid form is as follows:

(SEQ ID NO: 5)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg

The 1-44 and 1-29 forms differ in that the 1-44 form contains the following additional amino acids, which correspond to positions 30-44 of the 1-44 form:

(SEQ ID NO: 6)
Gln-Gln-Gly-Glu-Ser-Asn-Gln-Glu-Arg-Gly-Ala-
Arg-Ala-Arg-Leu

In an embodiment, the above-mentioned GRF analog is a GRF analog of formula A:

X-GRF Peptide (A)

wherein;

the GRF peptide is a peptide of formula B;

(SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0 (B)

wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle;
A28 is Ser or Asn;
A30 is a bond or amino acid sequence of 1 up to 15 residues; and
R0 is NH$_2$ or NH—(CH$_2$)n-CONH$_2$, with n=1 to 12; and
X is a hydrophobic tail anchored via an amide bond to the N-terminus of the peptide and the hydrophobic tail defining a backbone of 5 to 7 atoms;
wherein the backbone can be substituted by C1-6 alkyl, C3-6 cycloalkyl, or C6-12 aryl and the backbone comprises at least one rigidifying moiety connected to at least two atoms of the backbone;
said moiety selected from the group consisting of double bond, triple bond, saturated or unsaturated C3-9 cycloalkyl, and C6-12 aryl.

In embodiments, X noted above is selected from the group consisting of:

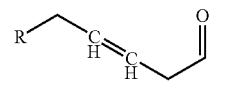

(R = H or CH$_3$ or CH$_2$CH$_3$)
cis or trans

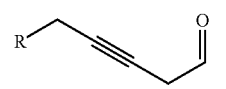

(R = H or CH$_3$ or CH$_2$CH$_3$)

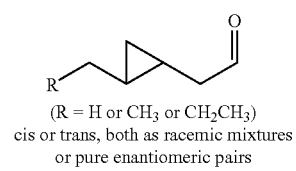

(R = H or CH$_3$ or CH$_2$CH$_3$)
cis or trans, both as racemic mixtures
or pure enantiomeric pairs

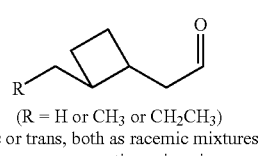

(R = H or CH$_3$ or CH$_2$CH$_3$)
cis or trans, both as racemic mixtures
or pure enantiomeric pairs

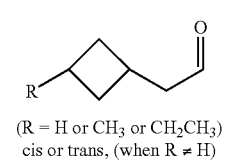

(R = H or CH$_3$ or CH$_2$CH$_3$)
cis or trans, (when R ≠ H)

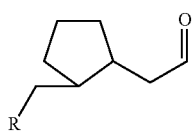

(R = H or CH₃ or CH₂CH₃)
cis or trans, both as racemic mixtures
or pure enantiomeric pairs

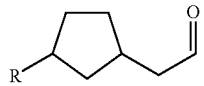

(R = H or CH₃ or CH₂CH₃)
cis or trans, (when R ≠ H)
both as racemic mixtures
or pure enantiomeric pairs

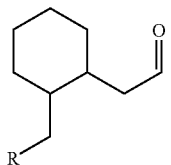

(R = H or CH₃ or CH₂CH₃)
cis or trans, both as racemic mixtures
or pure enantiomeric pairs

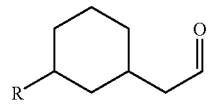

(R = H or CH₃ or CH₂CH₃)
cis or trans, (when R ≠ H)
both as racemic mixtures
or pure enantiomeric pairs

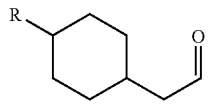

(R = H or CH₃ or CH₂CH₃)
cis or trans, (when R ≠ H)

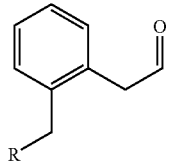

(R = H or CH₃ or CH₂CH₃)

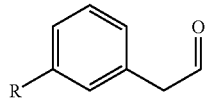

(R = H or CH₃ or CH₂CH₃)

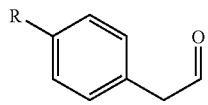

(R = H or CH₃ or CH₂CH₃)

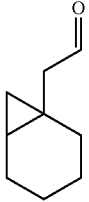

In embodiments, A30 noted above is selected from the group consisting of:
(a) a bond;
(b) an amino acid sequence corresponding to positions 30-44 of a natural GRF peptide, and
(c) said amino acid sequence of (b) having a 1-14 amino acid deletion from its C-terminal.

In embodiments, the above-noted GRF peptide is selected from the group consisting of:
(a) a polypeptide comprising the amino acid sequence of SEQ ID NO: 3;
(b) a polypeptide comprising the amino acid sequence of SEQ ID NO: 5; and
(c) the polypeptide of (a) having a 1 to 14 amino acid deletion from its C-terminus.

In an embodiment, the above-noted GRF analog is (hexenoyl trans-3)hGRF(1-44)NH₂.

Methods of preparing the above-described GRF analogs are described in U.S. Pat. No. 5,861,379 (Ibea et al., Jan. 19, 1999); U.S. Pat. No. 6,020,311 (Brazeau et al., Feb. 1, 2000), U.S. Pat. No. 6,458,764 (Gravel et al., Oct. 1, 2002) and published US application No. 2004/0171534 A1 (Gravel et al., published Sep. 2, 2004).

As noted above, in various embodiments, the above-mentioned GH secretagogue may be used therapeutically in formulations or medicaments to effect the above-noted alterations and to prevent or treat the above-noted conditions. The invention provides corresponding methods of medical treatment, in which a therapeutic dose of a GH secretagogue is administered in a pharmacologically acceptable formulation, e.g. to a patient or subject in need thereof. Accordingly, the invention also provides therapeutic compositions comprising a GH secretagogue and a pharmacologically acceptable excipient or carrier. In one embodiment, such compositions include GH secretagogue in a therapeutically or prophylactically effective amount sufficient to effect the above-noted alterations and to treat the above-noted conditions. The therapeutic composition may be soluble in an aqueous solution at a physiologically acceptable pH.

A "therapeutically effective amount" refers to an amount effective, at dosages and for periods of time necessary, to achieve the desired therapeutic result, such as to effect the above-noted alterations and to reduce the progression of the above-noted conditions. A therapeutically effective amount of a GH secretagogue may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of onset or progression of the above-noted conditions. A prophylactically effective amount can be determined as described above for the therapeutically effective amount. For any particular subject, specific dosage regimens may be adjusted over time according to the individual need and the professional judgement of the person administering or supervising the administration of the compositions.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, subcutaneous, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a GH secretagogue can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a GH secretagogue) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a GH secretagogue may be formulated with one or more additional compounds that enhance its solubility.

In accordance with another aspect of the invention, therapeutic compositions of the present invention, comprising a GH secretagogue, may be provided in containers, kits or packages (e.g. commercial packages) which further comprise instructions for its use to effect the above-noted alterations and to prevent or treat the above-noted conditions.

Accordingly, the invention further provides a package comprising a GH secretagogue or the above-mentioned composition together with instructions to effect the above-noted alterations and to prevent or treat the above-noted conditions.

The invention further provides a use of a GH secretagogue to effect the above-noted alterations and to prevent or treat the above-noted conditions. The invention further provides a use of a GH secretagogue for the preparation of a medicament to effect the above-noted alterations and to prevent or treat the above-noted conditions.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

Throughout this application, various references are referred to describe more fully the state of the art to which this invention pertains. The disclosures of these references are hereby incorporated by reference into the present disclosure.

EXAMPLES

Example 1

Study Drug

The compound used in the studies below is (hexenoyl trans-3)hGRF(1-44)NH$_2$ (also referred to as TH9507 herein), which is a synthetic human growth hormone releasing factor analog that comprises the 44-amino acid sequence of human growth hormone releasing factor (hGRF) on which a hexenoyl moiety, a C6 side chain has been anchored on Tyr 1 at the n-terminal. (hexenoyl trans-3)hGRF(1-44)NH$_2$ or Th9507 has the following structure:

```
                                                (SEQ ID NO: 7)
(trans)CH3-CH2-CH=CH-CH2-CO-Tyr-Ala-Asp-Ala-Ile- Phe-Thr-Asn-Ser-Tyr-Arg-Lys-Val-Leu-Gly-Gln-Leu- Ser-Ala-Arg-Lys-Leu-Leu-Gln-Asp-Ile-Met-Ser-Arg- Gln-Gln-Gly-Glu-Ser-Asn-Gln-Glu-Arg-Gly-Ala-Arg- Ala-Arg-Leu-NH2
```

(hexenoyl trans-3)hGRF(1-44)NH$_2$ was synthesized via the methods set forth in U.S. Pat. No. 5,861,379 (Ibea et al.; Jan. 19, 1999).

The in vitro half-life of Th9507 is 3-8 hours compared to 0.56 hours for hGRF. Daily 1 and 2 mg doses have been shown to increase IGF-I to the physiological range seen in younger adults (14). The safety profile of TH9507 is generally good. Th9507 has been studied in patients with Type II DM, and was not shown to aggravate overall glycemic control when administered at a daily dose up to 2 mg (15).

Example 2

Administration of TH9507 for Improving Daytime Vigilance in Subjects with Sleep Maintenance Insomnia The present example shows the effect of a 14 day-administration of 2 doses of TH9507 (0.1 mg and 1 mg) on vigilance parameters in subjects of 35 to 50 years of age exhibiting sleep maintenance insomnia.

Material and Methods

The study involved 82 patients exhibiting sleep maintenance insomnia (20 females, 62 males; mean age 43.2±5.4 years). Patients were selected based on the Pittsburgh Sleep Quality Index (Score ≧5), the Walters Criteria for Sleep Maintenance Insomnia, and the Beck Questionnaire (Score ≦17). The primary exclusion criteria were other primary sleep disorders and the use of any products affecting sleep or vigilance in the 30 days prior to entering the study.

The study was a randomized, double-blind, placebo-controlled, parallel group and multicenter evaluation of two doses of TH9507 (0.1 mg and 1 mg) administered daily by subcutaneous injection at bedtime for 14 consecutive days. To evaluate vigilance and the performance in the morning, patients underwent a battery of cognitive tests including the Continuous Performance Test (CPT) at baseline and at the end of treatment period.

The CPT has been described in the literature as a measure of consistency in responding and ability to sustain attention over time (Aleman A, et al., *J Clin Endocrinol Metab* 1999 84(2):471-475). This test required subjects to press space bar each time the letter "A" was followed by "X". Omission and commission errors, and Mean Reaction Time of correct responses were analyzed.

Results

Demographic characteristics by treatment group are displayed in the following table:

TABLE 1

Demographic (screening) data by treatment groups

|  | Placebo N = 29 | 0.1 mg N = 26 | 1 mg N = 27 | P value |
|---|---|---|---|---|
| Age |  |  |  |  |
| (Mean ± SD) | 44.0 ± 5.8 | 43.2 ± 5.8 | 42.3 ± 4.5 | 0.53 |
| (range) | (35-56) | (34-60) | (34-50) | (F-test) |
| Gender |  |  |  |  |
| Males | 21 | 19 | 22 | 0.68 |
| Females | 8 | 7 | 5 | chi-square test |
| Weight (kg) |  |  |  | 0.94 |
| (Mean ± SD) | 78.0 ± 14.3 | 78.2 ± 12.4 | 79.3 ± 15.3 | (F-test) |

As illustrated in FIG. 1, the Mean Reaction Time of the CPT was significantly and markedly decreased in the 0.1 mg group when compared to placebo. The decrease from baseline to day 9 was 45.85 ms (P=0.023 when compared to placebo as analyzed by an ANOVA model). No significant effect was observed in the 1 mg group. Circulating IGF-1 and IGFBP-3 levels were significantly increased at week 2 in the 1 mg group when compared to placebo (P<0.0001, ANOVA on changes from baseline). As expected the 0.1 mg did not affect these parameters (P=0.07 and P=0.99) for IGF-1 and IGF-BP3 respectively, ANOVA model on changes from baseline).

Additional data on effects of TH9507 on vigilance obtained in a previous study are presented in FIG. 2. In this study, TH9507 was administered daily for 7 days in a crossover design. This study involved 12 healthy subjects aged between 50 to 65 years, exhibiting age-related sleep impairment (Pittsburgh Sleep Quality Index Score from 3 to 7). At the end of the treatment period, daytime vigilance was significantly enhanced when compared to placebo in subjects receiving 1 mg of TH9507, as assessed by P300, an event-related potential test. Changes from Baseline to day 9 in the Pz amplitude of the Evoked Related Potential (P300) observed in the placebo and 1 mg group were as follows: Placebo, −15%; 1 mg, +55%, P=0.0114, as analyzed by an ANOVA model.

In both studies, the safety profile of TH9507 was comparable to that of the placebo, except for a higher incidence of reactions at the site of injection observed at 1 mg in the insomnia study.

In summary, these results provide evidence that TH9507 improves daytime vigilance in sleep maintenance insomnia in subjects and would favor a direct mechanism of action of TH9507, not mediated by IGF-1. Data are supported by those obtained by Vitiello et al (Vitiello M. V., et al., *Gerontologist* 2002 40 (Special Issue 1):39-N/A. using hGRF in cognitive tests involving psychomotor and perceptual processing speed (Deijin J B et al, *Psychoneuroendocrinology* 1998 23(1):45-55) and may support further clinical investigations in subjects with impaired cognitive functions.

Example 3

Effects of TH9507 on the Immune Response to Influenza Vaccination in Elderly Subjects The present example describes immune findings following an influenza vaccination challenge in elderly subjects.

Material and Methods

Eighty seven (87) subjects aged 75 years in average were included in a double-bind, randomized, placebo-controlled study. TH9507 or a placebo was administered at a daily dose of 1 or 2 mg by subcutaneous injection for 8 weeks. Follow-up assessments were conducted for 12 weeks after the end of the treatment period. At week 4, in the middle of the treatment period, subjects received the commercial Canadian influenza vaccine (Vaccine Fluviral® S/F, Shire, Montreal, Canada) containing 15 μg each of A/New Caledonia/20/99, A/Panama/2007/99, B/Victoria/504/2000 antigens.

Influenza-specific proliferative T cell response and antibody titers were evaluated for each of the 3 strains contained in the vaccine. The proliferative T cell response was assessed by a mitogen assay using tritiated thymidine ($^3$H) incorporation and results were log-base 10 transformed prior to analysis. The antibody titers were determined by standard hemaglutinaion inhibition assay and results were log-base 2 transformed prior to analysis.

Eighty one (81) subjects completed the study as per protocol. Subject demographics are shown in the following table:

TABLE 2

Subject demographics

|  | Placebo | 1 mg TH9507 | 2 mg TH9507 | All | P-value |
|---|---|---|---|---|---|
| Age (years) | 75.9 ± 6.5 | 74.9 ± 6.1 | 73.2 ± 4.4 | 74.6 ± 5.8 | 0.21 |
| Total N | 29 | 29 | 29 | 187 | 0.96 |
| Female | 13 | 13 | 14 | 40 | |
| Male | 16 | 16 | 15 | 47 | |
| BMI (kg/m$^2$) | 27.4 ± 5.8 | 26.9 ± 4.2 | 29.2 ± 6.0 | 27.8 ± 5.4 | 0.26 |

Data for age and BMI are presented as mean ± SD. Baseline comparability among treatment groups was tested by ANOVA (age, BMI) or Pearson's chi-square test (gender).

Results

As shown in FIG. 3 the mean AUC calculated for the whole study period including both the treatment and follow-up period (week 0 to week 20) was statistically higher in the 2 mg group when compared with placebo (Panama, P=0.03; New Caledonia, P=0.001; Victoria, P=0.02, (Pairwise comparisons for difference among treatment groups and ANCOVA analysis for overall treatment significance).

Figure 4:
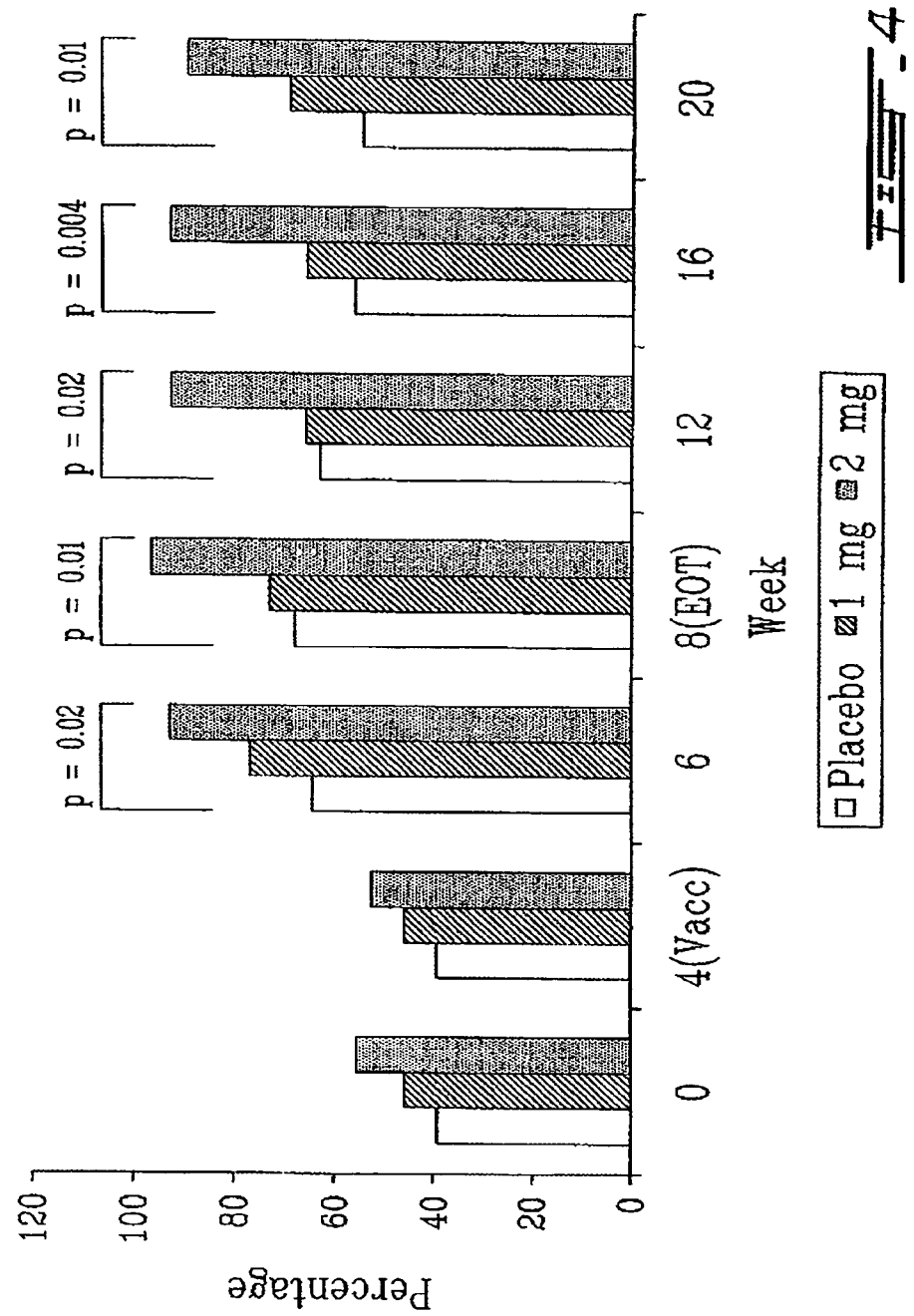
FIG. 4 illustrates the percentage of subjects with protective antibody titers (>1/40) for B/Victoria.

As illustrated in FIG. 4, administration of TH9507 increased the proportion of patients achieving a protective antibody level for the Victoria antigen when compared to placebo. This observation reached statistical significance at the 2 mg dose and was noted during both the treatment and the follow-up periods (week 6: P=0.02; Week 8: P=0.01; week 12: P=0.02; week 16; P=0.004, week 20: P=0.01, pairwise comparisons for difference among treatment groups and Pearson chi-square test for overall treatment difference) indicating a sustained effect for up to 16 weeks after cessation of treatment. No statistical difference in the percentage of subjects was observed in the Panama and New Caledonia strains.

A dose-related increase in the mean IGF-1 values was observed during the whole treatment period in both Th9507 groups when compared to baseline. Values returned to baseline following cessation of treatment.

No major difference in the incidence of adverse events was observed between treatment groups except for a dose-related trend in the incidence of reactions at the site of injection.

In summary, the findings observed in this study strongly indicate that TH9507 has a therapeutic potential in immune indications. In particular, its effect of the T-lymphocyte proliferation response following vaccination makes it attractive to develop in clinical situations where the cell-mediated immune system is depressed, such as viral infections in the elderly and immune-deficient states following HIV infection, high-dose chemotherapy or radiotherapy.

Example 4

ThGRF's Benefits in Wasting/Catabolic Conditions

The present example shows the effect of a 7-day administration of TH9507 on circulating IGF-1 levels in healthy middle-aged men.

Material and Methods

The study used a randomized, double-blind, placebo-controlled design and was conducted in healthy men, aged 50 to 60 years old. Subjects (8 per group) were injected S.C. once a day for 7 consecutive days with placebo, 0.5, 1 or 2 mg of TH9507. Circulating IGF-1 levels were measured on Days 1 to 7. The 12 hour GH response and TH9507 PK profile were determined on Day 1 and 7.

Results

Figure 5:
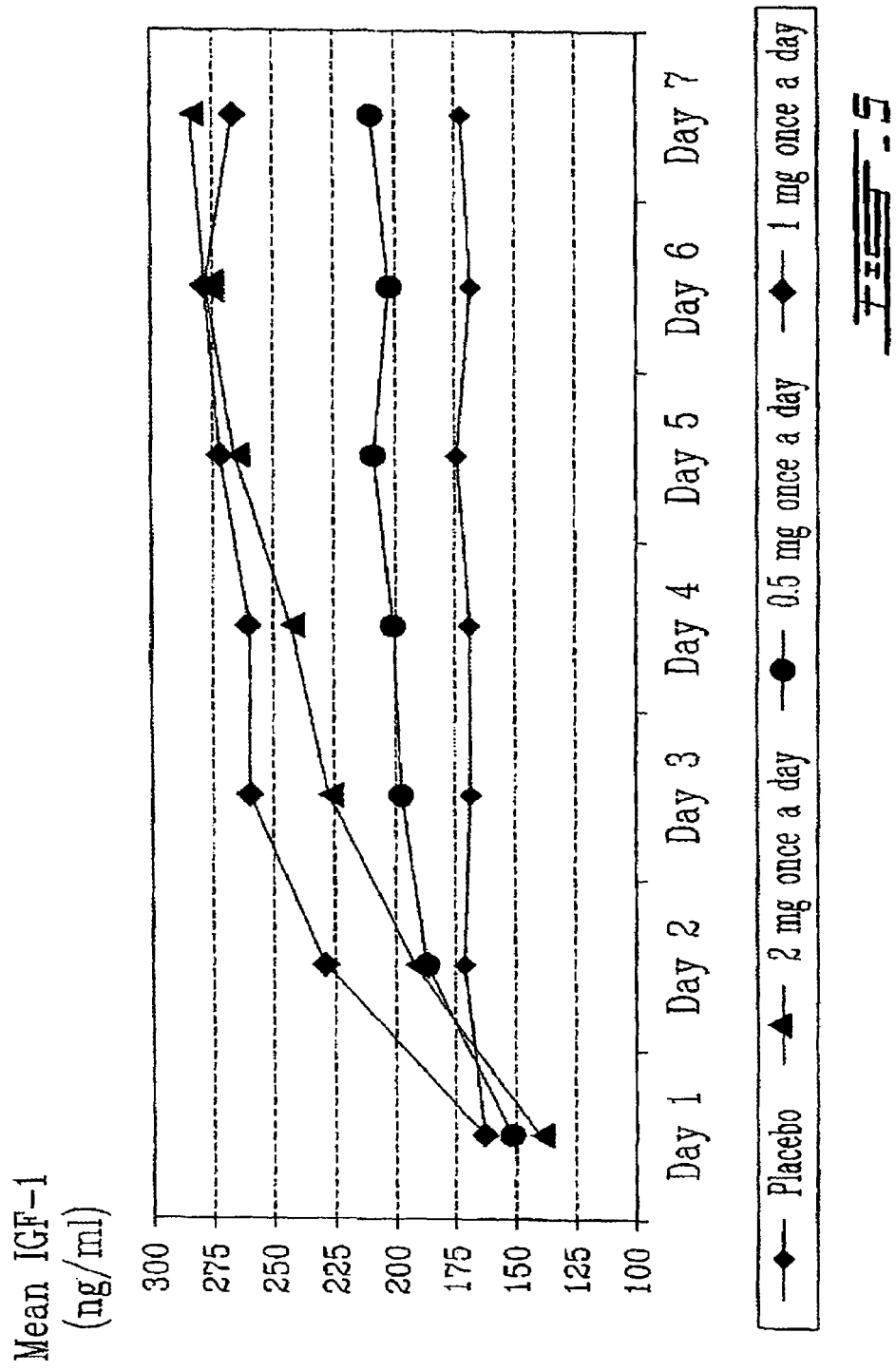
FIG. 5 illustrates the variation of mean IGF-1 levels during time with placebo, 2 mg/day TH9507, 0.5 mg/day TH9507 and 1 mg/day TH9507.

As shown in FIG. 5, IGF-1 increased over baseline values by 8% (placebo), 37% (0.5 mg), 89% (1 mg) and 106% (2 mg); these increases were statistically significant for all 3 doses of TH9507. The 1 mg and 2 mg doses were equally potent and induced a doubling of IGF-1 levels up to levels expected for young adults (286±25 and 284±55 ng/ml, respectively), none of the subjects exhibited levels greater than 400 ng/ml. A plateau was reached at Day 4 and 6 for the 1 mg and 2 mg doses, respectively.

GH response to TH9507 increased rapidly both on Days 1 and 2. The increase was dose dependent between the 0.5 and 1 mg dose (P<0.01), and was similar at the 1 mg and 2 mg doses. No significant modification in prolactin, ACTH, cortisol, TSH, LH or FSH was observed following single or repeated treatment with TH9507.

PK analysis indicated that Cmax and AUC parameters increased in function of the dose administered. The half-life of the TH9507 ranged between 2 and 5 hours.

These results clearly indicate that TH9507 is highly specific on GH secretion and a powerful IGF-1 inducer, suggesting potential clinical benefits in wasting/catabolic conditions.

Example 5

Effects of GRF on Non-HDL Cholesterol in Patients with Type 2 Diabetes

The present example illustrates beneficial effects of TH9507 on non-HDL cholesterol levels in a diabetic population.

Material and Methods

A double-blind placebo-controlled study was conducted in 53 type II diabetic patients (age=61±7 [SD]; 34% female) on stable antidiabetic medication (26% on insulin). Patients were randomized to parallel groups to receive daily subcutaneous administration of a placebo, 1 mg or 2 mg TH9507, respectively.

Results

A statistically significant difference was observed at Week 12 between the 3 treatment groups in the mean total cholesterol change from baseline (P=0.04). Values decreased in the 2 mg group (−11.1±21.9 mg/dl; −6%), as compared to increases in the Placebo (+9.7±22.6 mg/dl; +5%) and 1 mg group (+6.1±16.2 mg/dl; +3%). This effect was accompanied by a decrease in the mean non-HDL cholesterol values in the 2 mg group (−10.1±19.0 mg/dl; −7%) and increases in the placebo (+6.8±17.8 mg/dl; +5%) and 1 mg group (+3.8±15.5 mg/dl; +3%).

No statistically significant differences were observed between the three groups during the treatment period in terms of insulin relative response to an oral glucose tolerance test. At Week 12, glycosylated hemoglobin (HbA1c) levels displayed a trend for a decrease in the placebo group, a decrease in the 1 mg group, and no change in the 2 mg group. Clinically relevant changes in antidiabetic medications occurred with a similar incidence in the three treatment groups.

A dose-related increase in the IGF-1 levels was observed at the end of the treatment period.

In summary, this study indicates that the repeated administration of TH9507 for 12 weeks decreases the total and non-HDL cholesterol fraction in diabetic subjects and can be safely administered to this population without impairing glucose control. The effects observed on blood lipids and the known lipolytic properties of GH warrant the investigation of TH9507 for the treatment of syndromes associated with visceral fat accumulation.

Example 6

Effect of GRF Analog on Lipid Profile, Body Composition and Quality of Life in HIV-Infected Patients This study investigated the effects of TH9507, on abdominal fat accumulation associated with HIV lipodystrophy.
Design: Randomized, placebo-controlled, multi-center, dose ranging (placebo, 1 mg or 2 mg SC QD), parallel group, 12-week study
Patients: 61 HIV-infected patients (BMI 28±3 [SD] kg/m$^2$, 28% diabetic or glucose intolerant) with increased waist circumference (102 cm±8 [SD]) and waist/hip (1.0±0.1 [SD])
Measurements: Body composition was assessed by DXA and abdominal CT scan; IGF-I, insulin, glucose, lipid, bone turnover, immunologic, and safety parameters.
Results: Treatment with TH9507 resulted in a dose-related increase in serum IGF-1 levels within the physiological range [18 (32) ng/mL, 87 (67) ng/mL, 123 (79) ng/mL, mean (SD) for placebo, 1 mg, 2 mg, respectively, P<0.01 for change in each active group vs. placebo]. Lean body mass increased significantly in both treatment groups compared to placebo [−0.5 (1.6) kg, 0.7 (2.0) kg, and 1.7 (2.3) kg; placebo, 1 mg, 2 mg, respectively; P<0.01 for 2 mg dose vs. placebo, P<0.05 for the 1 mg group vs. placebo]. Trunk fat decreased in the 2 mg group compared to placebo (0.8%, −4.6% and −9.2%; placebo, 1 mg, 2 mg, respectively, P=0.01 for 2 mg vs. placebo), with no significant change in limb fat. Visceral fat decreased most in the 2 mg group (−5.4%, −3.6% and −15.7%; placebo, 1 mg, 2 mg, respectively; P=0.03 for change within 2 mg group but P=NS vs. placebo) whereas subcutaneous fat was preserved and did not change between or within groups. The ratio of VAT:SAT improved significantly in both treatment groups compared to placebo (−0.01 (0.10), −0.23 (0.47) and −0.14 (0.18), P<0.01 for the 2 mg group vs. placebo and P<0.05 for the 1 mg group vs. placebo. Triglyceride and the cholesterol to HDL ratio decreased significantly in the 2 mg treatment group compared to placebo. Treatment was generally well-tolerated without changes in either fasting glucose or 2-hour OGTT.
Conclusion: TH9507 effectively improved body composition and reduced truncal fat by preferentially decreasing visceral fat while preserving subcutaneous fat in patients with HIV lipodystrophy. TH9507 did not increase glucose levels, even among those with impaired glucose tolerance or diabetes mellitus at baseline, and improved the lipid profile. These data suggest that TH9507, a GRF analog, may be a beneficial treatment strategy for HIV lipodystrophy.
Methods
Subjects Eighty-eight subjects were screened between May 2003 and November 2003. Sixty-one subjects were enrolled. HIV infected males age 18-65 years and non-menopausal females age >18 years with visceral fat accumulation considered to be part of the HIV lipodystrophy syndrome, waist circumference ≧95 cm for men and ≧94 cm for women, and a waist to hip ratio ≧0.94 for men and ≧0.88 for women were enrolled. We excluded, subjects with a BMI ≦20 kg/m2, CD4 cell count ≦100 cells/mm$^3$, viral load ≧10,000 copies/mL, history of opportunistic infection or HIV-related disease within 3 months of the study, history of prostrate cancer or PSA >5 ng/ml in male subjects, history of breast cancer or abnormal mammography within 6 months of the study (for these patients without a mammogram within this time frame, one was performed as part of the study) in female subjects, known hypopituitarism or history of pituitary surgery, radiation or significant head trauma, untreated hypothyroidism, prior history of Type I diabetes mellitus (DM), any prior use of GH or GH related products, experimental or marketed, within 6 months of the study, systemic steroid administration or megestrol acetate within 60 days of the study, fasting glucose >150 mg/dL, SGOT or SGPT >3× upper limit of normal, creatinine >1.5× upper limit of normal, or hemoglobin <9 g/dL. Subjects receiving testosterone or estrogen within the prior six months, with known drug or alcohol dependence or who had participated in another clinical trial with an investigational agent within 30 days were also excluded from the study. All subjects were required to be on a stable antiretroviral regimen for 8 weeks prior to enrollment. Subjects receiving lipid lowering medications were required to be on a stable regimen for 3 months prior to enrollment. Subjects were not permitted to begin antidiabetic medication, use systemic corticosteroids for >10 days, or begin estrogen or testosterone preparations during the study.
Study Procedures Subjects underwent a screening visit to determine eligibility. All subjects gave written consent to participate in the study, and the study was approved by the Institutional Review Board at each participating site. BMI, anthropometric measurements, TSH and prolactin were performed. Viral load and CD4 count were performed if not previously done within 8 weeks of the study. A PSA was performed in male subjects and a pregnancy test was performed in female subjects. Mammography was also performed in female subjects if not previously done within 6 months of the study.

At the baseline visit, anthropometric measurements were obtained. Total body lean and fat mass as well as regional fat mass in the trunk and extremities were assessed by DEXA. Abdominal subcutaneous and visceral fat area and the ratio of VAT to SAT were determined by cross-sectional CT at L4-L5. Biochemical parameters including insulin-like growth factor-I, glucose, insulin, lipid profile (cholesterol, HDL, LDL, triglyceride, non HDL and the ratio of cholesterol:HDL), free fatty acids, HbA1C, IGFBP-3, and bone markers (serum osteocalcin and NTX-1), CD4, viral load, and a pregnancy test for female subjects were determined in the fasting state. In addition, insulin and glucose response to a 75 gram standard glucose challenge were assessed and a quality of life questionnaire was administered.

After baseline evaluations were complete subjects were randomized equally to one of three groups, placebo, 1 mg TH9507 or 2 mg TH9507. Randomization was performed by an independent consulting firm, using a permuted block algorithm, with block size equal to 3 and kept confidential in the Theratechnologies Quality Assurance Department until unblinding. Subjects were stratified for gender at the time of treatment assignment. Treatment assignment was blinded to investigators and patients. Active drug and placebo (mannitol) were provided as lyophilized powder in vials of identical appearance, each containing 1.1 mg of material. Each vial was reconstituted with sterile water immediately prior to injection. Patients were instructed to inject each AM at approximately 0900 h.

Subjects returned for a safety visit at Week 1 to assess adverse events and compliance. Subjects returned at 2 weeks to assess weight, anthropometric measures, lipid profile, free fatty acid, IGFB-1, IGFBP-3, glucose, adverse events and compliance. Subjects returned for a visit at week 6 identical to baseline and a visit at week 9 to assess compliance and adverse events. Subjects returned for a last study visit at week 12—or, whenever possible, at the time of early termination—identical to the baseline visit.

Study Drug

TH9507 was used in this study, as noted above.

Methods

Biochemical Indices

Clinical laboratory testing was performed by a central lab. Serum IGF-1 was measured after acid-ethanol extraction using the Esoterix RIA kit (Esoterix Inc., Calabasas Hill, Calif.), with a sensitivity of 10 ng/mL. Intra- and inter-assay coefficients of variation were 4.6-20% and 9-10%, respectively. Serum IGFBP-3 was measured using the Esoterix RIA kit (Esoterix Inc., Calabasas Hill, Calif.) with a sensitivity of 0.3 mg/mL. Intra- and inter-assay coefficients of variation were 5.1-13% and 5.5-17%, respectively. HDL, LDL, total cholesterol, triglycerides and FFA were determined by enzymatic calorimetric assay. Glucose was measured by enzymatric test (Gluco-Quant®, Roche diagnostics, Indianapolis, Ind.). HbA1c was determined by chromatography. PSA was determined using the Hybritech®PSA test (Beckman Coulter, Mississauga, Canada). TSH was measured by microparticle enzyme immunoassay (AxSYM hTSH II, Abbott Laboratories, Abbott Park, Ill.). NTX (N-terminal telopeptide of type I collagen; a bone resorption marker) was measured by ELISA using a commercially available kit (Osteomark™, Ostex International Inc., Seattle, Wash.). Osteocalcin was measured using a commercially available enzymatic immunoassay kit (Metra™ osteocalcin, Quidel Corporation, San Diego, Calif.). CD4 and viral load were performed by the individual site labs by routine methodology.

HOMA was calculated as:

$$\left[\frac{\Delta \text{ Insulin } (30 \text{ min} - 0 \text{ min})}{\Delta \text{ Glucose } (30 \text{ min} - 0 \text{ min})}\right] / \text{Insulin } (0 \text{ min}).$$

Body Composition

Whole body and regional DEXA (dual energy X-ray absorptiometry) and cross-sectional abdominal CT scans were performed at the individual study sites based on previously established protocols and were standardized across sites. Digitized images were sent to a central reading center, St. Lukes Roosevelt Hospital, for analysis by independent experts without knowledge of treatment assignment. Each site was given a procedure manual to follow in obtaining the body composition data and was certified in the proper technique. For the CT scans, parameters were standardized as follows: Tube Voltage=120 kV, Tube Current=250 mA, Exposure=375 mAs, matrix 512×512. DFOV was set to include the entire slice into the field of view. For the DEXA scans total body scans were performed with analysis of lean body mass, total fat mass, and regional fat mass in the trunk and extremities as previously described (16). After analysis the data was transferred to the data management center and incorporated in the study database.

Statistics

Body composition endpoints included trunk fat and trunk to limb fat ratio by DEXA and VAT and VAT:SAT by CT scan. Other endpoints included IGF-I, lipid parameters, glucose and insulin, CD4, viral load, bone markers, and quality of life. A sample size of 20 patients/group was planned to assess a statistically significant change of 10% or more in intra-group analyses. The planned dropout rate was 25% and therefore 60 patients were enrolled into the study. Baseline data are compared between the groups by F-test based on ANOVA for continuous variables and Chi-Square test for categorical variables. Change over time between groups is compared by ANOVA or the Chi-Square test. Where appropriate, data were rank transformed prior to analysis. Changes within each group are determined by t-test. The ITT (intent to treat) population is defined as all subjects who received at least one dose of the study treatment. Descriptive statistics and analyses for all efficacy and safety analyses are performed on the ITT population. End of study, 12 week, data are used to calculate changes in body composition. For biochemical indices, the last observation available is used to calculate change. Imputation for missing data is not performed. For body composition, end of study data are used to calculate change. Interim analyses were not performed. Results are mean (SD) unless otherwise noted. All statistical tests were performed with a two-sided Type I error level of 0.05.

Results

Figure 6:
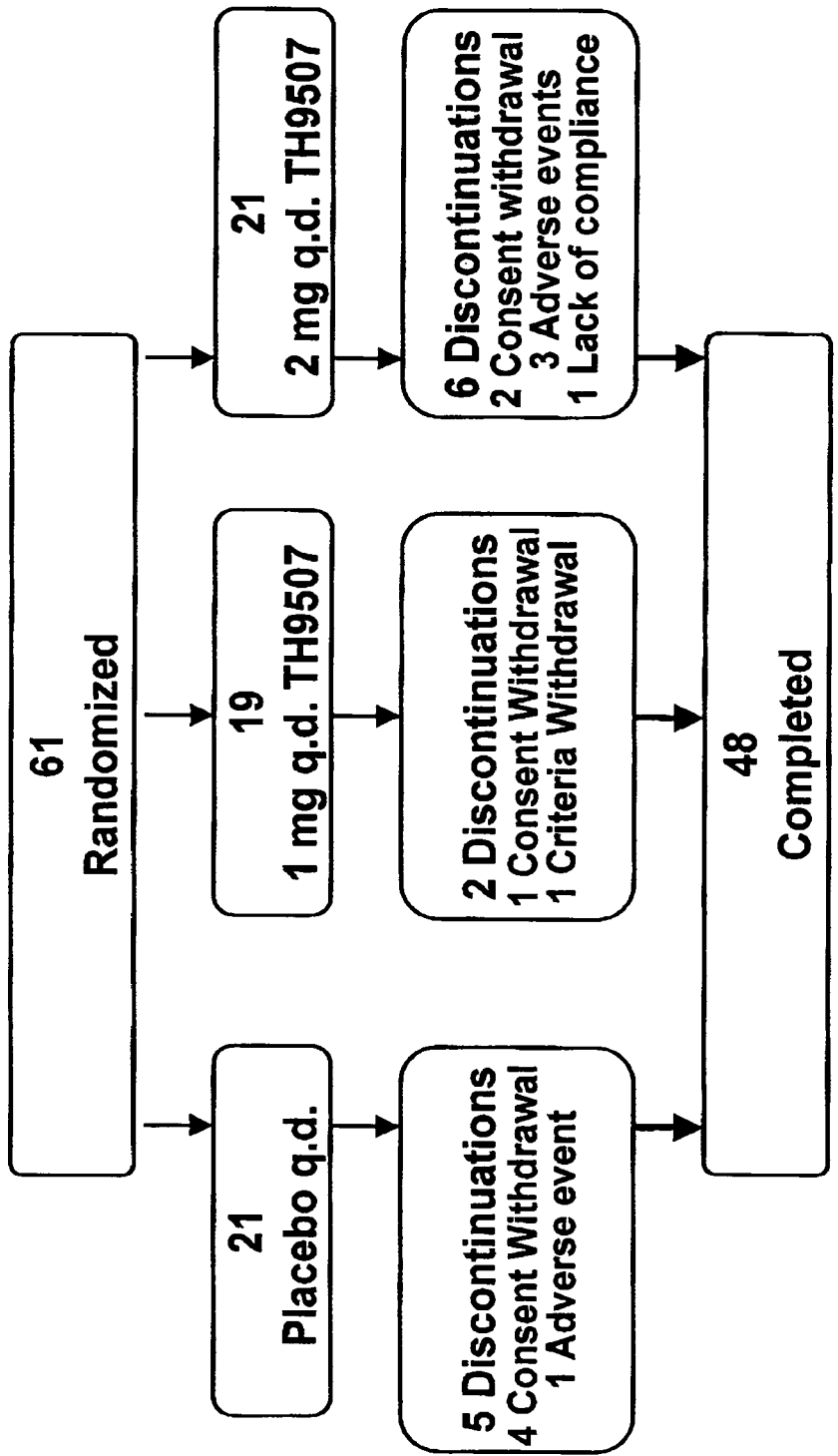
FIG. 6 illustrates a flow diagram of patient disposition in respect of the studies described in Example 6.
Figure 7:
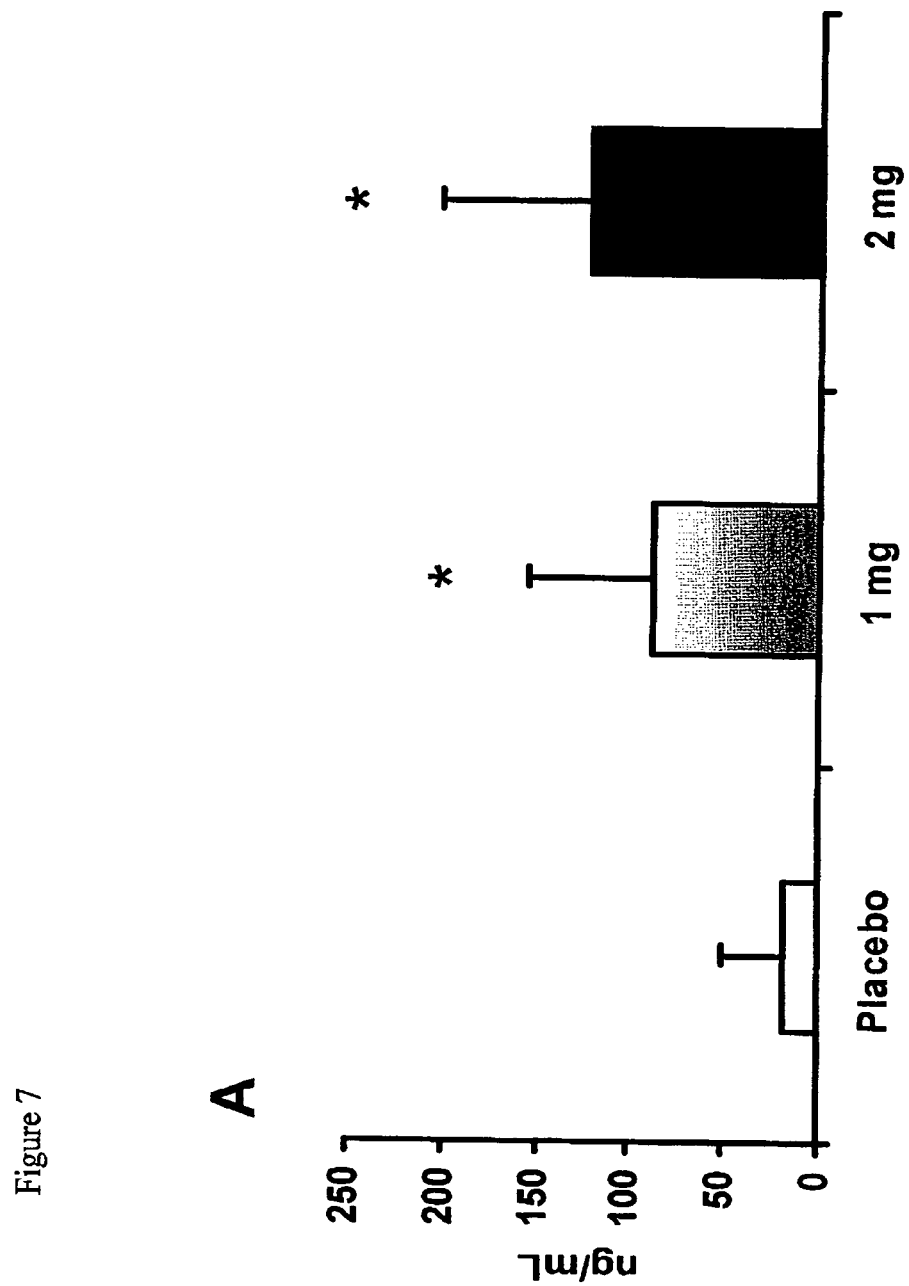
FIG. 7 illustrates results of dose response of TH9507 on A) IGF-I and B) truncal fat, as measured by DEXA, as described in Example 6. 7A: "ng/ml" represents ng/ml of IGF-1 as measured. 7B: "kg" represents change in truncal fat, with the negative values indicating a decrease in truncal fat. 7A and 7B: "placebo", "1 mg" and "2 mg" correspond to administration of a placebo, 1 mg of Th9507 and 2 mg of Th9507, respectively. Results are mean (SD). *=P<0.01 vs. placebo by ANOVA.

Sixty-one subjects were randomized, 21 to placebo, 19 to TH9507 1 mg and 21 to TH9507 2 mg. Five subjects discontinued in the placebo group, 2 in the 1 mg group and 6 in the 2 mg group, for a 79% completion rate. See FIG. 6 for patient disposition and flow diagram.

Baseline demographic for the three study groups are shown in Table 3. At baseline no significant differences were seen between the groups except, including use of antiretroviral therapy. The percentage of patients with diabetes (fasting glucose $\geq 7.0$ mmol/L or 2h-glucose $\geq 11.1$ mmol/L) and impaired glucose tolerance (6.1 mmol/L $\leq$ fasting glucose $\leq 6.9$ mmol/L or 7.8 mmol/L $\leq$ 2h-glucose $<11.1$ mmol/L) was not different between the groups. Among the entire study group, 23% of subjects demonstrated IGT and 5% demonstrated diabetes mellitus at baseline.

TABLE 3

Baseline Characteristics

|  | Placebo | 1 mg | 2 mg | P |
|---|---|---|---|---|
| Age | 46.1 (7.4) | 46.5 (6.4) | 44.6 (7.1) | 0.64 |
| Gender |  |  |  |  |
| Males/Females | 18/3 | 18/1 | 18/3 | NA |
| Ethnic origin |  |  |  |  |
| Cauc./Other | 18/3 | 15/4 | 17/4 | 0.84 |
| BMI | 28.9 (2.7) | 28.0 (3.2) | 27.3 (4.1) | 0.30 |
| WHR | 1.0 (0.1) | 1.0 (0.0) | 1.0 (0.1) | 0.65 |
| WC | 103.4 (8.0) | 100.3 (6.1) | 100.7 (9.1) | 0.40 |
| IGT-Diabetes | 7 | 4 | 6 | NA |

Data are mean (SD).
BMI, body-mass index;
WHR, waist/hip ratio;
WC, waist circumference Body Composition Lean body mass increased in both treatment groups compared to placebo [−0.5 (1.6) kg, 0.7 (2.0) kg, and 1.7 (2.3) kg, mean (SD) for placebo, 1 mg, 2 mg, respectively, P<0.01 for change in 2 mg group vs. placebo, P<0.05 for the change in 1 mg group vs. placebo, Table 3). Total fat decreased in the 2 mg group compared to placebo [0.3 (1.7) kg, −0.4 (1.8) kg and −1.4 (2.0) kg, placebo, 1 mg, 2 mg, respectively, P=0.01 for 2 mg group vs. placebo). Trunk fat decreased in the 2 mg group compared to placebo (0.8%, −4.6% and −9.2%, placebo, 1 mg, 2 mg, respectively, P=0.01 for 2 mg group vs. placebo) (FIG. 2). VAT tended to decrease more in the 2 mg group (−5.4%, −3.6% and −15.7%, placebo, 1 mg, 2 mg, respectively), (P=NS for comparison of 2 mg vs. placebo, P=0.03 for change within 2 mg group). SAT did not change significantly between the groups and the ratio of VAT:SAT decreased more in the treatment groups compared to placebo [0.01 (0.10), −0.23 (0.47), −0.14 (0.18)] (Table II) (P<0.01 for 2 mg vs. placebo and P=0.04 for 1 mg vs. placebo).

Biochemical Indices

IGF-I increased significantly with the 1 and 2 mg dose compared to placebo [18 (32) ng/mL, 87 (67) ng/mL, 123 (79) ng/mL, placebo, 1 mg 2 mg, respectively, P<0.01 for each active group vs. placebo] (FIG. 3). Triglyceride levels decreased in the 2 mg group compared to placebo (−0.2 (1.3), −0.9 (4.2), −0.9 (1.2), last observation values for placebo, 1 mg, 2 mg, respectively, P<0.05) and the ratio of cholesterol to HDL improved in both treatment groups compared to placebo (0.3 (1.1), −0.3 (0.7), −0.3 (0.6), last observation values for placebo, 1 mg, 2 mg, respectively, P<0.05).

Changes in fasting and 120 minute glucose were not significant between or within the treatment groups.

Bone Markers

Osteocalcin increased significantly within the 2 mg group, whereas no changes with NTX were seen (Table 4).

TABLE 4

Change from Baseline in Body Composition, Biochemical and Immunologic Parameters.

| | Placebo | | 1 mg | |
|---|---|---|---|---|
| | Baseline | Δ | Baseline | Δ |
| Body Composition | | | | |
| Lean Body Mass (kg) | 63.9 (9.8) | −0.5 (1.6) | 64.4 (10.0) | 0.7 (2.0) |
| Fat Mass (kg) | 22.1 (6.0) | 0.3 (1.7) | 19.0 (5.7) | −0.4 (1.8) |
| Trunk Fat (kg) | 14.6 (3.4) | 0.1 (1.1) | 13.1 (3.4) | −0.5 (1.4) |
| Limb Fat (kg) | 6.6 (2.8) | 0.1 (0.7) | 5.1 (2.6) | 0.1 (0.5) |
| VAT ($cm^2$) | 190.5 (75.7) | −12.0 (32.5) | 157.8 (56.6) | −11.9 (28.7) |
| SAT ($cm^2$) | 237.9 (85.2) | −10.5 (31.6) | 188.8 (89.0) | 6.8 (21.2) |
| VAT:SAT | 0.89 (0.50) | −0.01 (0.10) | 1.17 (1.25) | −0.23 (0.47)* |
| Biochemical Indices | | | | |
| GH Parameters[1] | | | | |
| IGF-1 (ng/mL) | 132.4 (42.4) | 18.3 (31.7) | 165.3 (62.3) | 87.5 (66.9)* |
| IGFBP-3 (Mg/L) | 2.7 (0.7) | 0.1 (0.4) | | 2.9 (0.9) |
| Lipid Parameters[1] | | | | |
| NONHDL Cholesterol (mmol/L) | 4.2 (1.0) | 0.3 (0.8) | 4.8 (2.1) | −0.4 (1.5) |
| Total Cholesterol (mmol/L) | 5.3 (1.0) | 0.4 (0.8) | 5.9 (2.3) | −0.4 (1.7) |
| LDL (mmol/L) | 3.2 (0.8) | 0.5 (0.8)* | 3.4 (0.9) | 0.1 (0.8) |
| HDL (mmol/L) | 1.1 (0.3) | 0.0 (0.1) | 1.1 (0.3) | 0.0 (0.2) |
| Triglycerides (mEq/L) | 3.1 (2.5) | −0.2 (1.6) | 3.9 (4.6) | −1.1 (4.4) |
| Chol:HDL | 4.9 (1.4) | 0.2 (0.8) | 5.5 (1.3) | −0.3 (0.6) |
| Glucose Parameters | | | | |
| Fasting Glucose (mmol/L) | 5.3 (0.6) | 0.2 (0.8) | 5.3 (0.8) | 0.1 (0.5) |
| $HBA_{1c}$ (%) | 5.1 (0.5) | −0.3 (0.5)* | 5.2 (0.4) | 0.2 (0.4)* |
| Two hour glucose (mmol/L) | 6.4 (2.9) | 0.6 (1.8) | 6.4 (2.4) | 0.1 (2.1) |
| Fasting Insulin (mUI/L) | 15.2 (18.0) | 5.1 (15.8) | 22.7 (30.7) | −2.8 (27.6) |
| HOMA-R | 3.7 (4.6) | 2.1 (5.5) | 5.5 (7.6) | 0.8 (7.0) |
| Bone Turnover Markers | | | | |
| Osteocalcin (ng/mL) | 9.2 (4.4) | 0.5 (3.9) | 8.0 (3.9) | 1.5 (4.8) |
| NTX (nMBCE/mM) | 36.3 (17.7) | −0.8 (20.8) | 37.1 (13.4) | 4.5 (24.9) |
| Immunologic Parameters | | | | |
| CD4 (cells/$mm^3$) | 540.9 (252.9) | 36.9 (107.6) | 525.4 (309.1) | 24.4 (147.41) |
| Viral load | | No stats available due to undetectable values | | |

| | 2 mg | | Week 12 | |
|---|---|---|---|---|
| | | | P value | P value |
| | Baseline | Δ | 2 mg vs. P | 1 mg vs. P |
| Body Composition | | | | |
| Lean Body Mass (kg) | 65.2 (6.9) | 1.7 (2.3)* | 0.0021 | 0.0467 |
| Fat Mass (kg) | 18.1 (7.6) | −1.4 (2.0)* | 0.0125 | 0.2962 |
| Trunk Fat (kg) | 12.2 (4.6) | −1.1 (1.3)* | 0.0144 | 0.1782 |
| Limb Fat (kg) | 5.1 (3.0) | −0.3 (0.8) | 0.1576 | 1.0000 |
| VAT ($cm^2$) | 160.2 (53.5) | −21.5 (27.9)* | 0.6428 | 1.0000 |
| SAT ($cm^2$) | 189.8 (124.3) | 4.4 (19.8) | 0.6919 | 0.3390 |
| VAT:SAT | 1.12 (0.74) | −0.14 (0.18)* | 0.0084 | 0.0434 |

TABLE 4-continued

Change from Baseline in Body Composition, Biochemical and Immunologic Parameters.

| | | | | |
|---|---|---|---|---|
| Biochemical Indices GH Parameters[1] | | | | |
| IGF-1 (ng/mL) | 157.0 (41.4) | 122.6 (79.1)* | 0.0002 | 0.0042 |
| IGFBP-3 (Mg/L) | 0.6 (0.7)* 2.9 (0.4) | 0.6 (0.5)* | 0.0007 | 0.0022 |
| Lipid Parameters[1] | | | | |
| NONHDL Cholesterol (mmol/L) | 4.0 (1.0) | −0.1 (0.7) | 0.0770 | 0.3067 |
| Total Cholesterol (mmol/L) | 5.2 (1.2) | −0.1 (0.8) | 0.1822 | 0.3175 |
| LDL (mmol/L) | 3.1 (1.0) | 0.2 (0.7) | 0.9533 | 0.3695 |
| HDL (mmol/L) | 1.2 (0.3) | 0.1 (0.1)* | 1.0000 | 1.0000 |
| Triglycerides (mEq/L) | 2.8 (1.8) | −0.9 (1.3)* | 0.0131 | 0.6146 |
| Chol:HDL | 4.3 (0.7) | −0.3 (0.7) | 0.0128 | 0.0508 |
| Glucose Parameters | | | | |
| Fasting Glucose (mmol/L) | 5.4 (0.6) | 0.1 (0.7) | 1.0000 | 1.0000 |
| $HBA_{1c}$ (%) | 5.2 (0.6) | −0.0 (0.5) | Contrasts not done (overall p = 0.008) | overall p = 0.0237 |
| Two hour glucose (mmol/L) | 6.4 (2.1) | 0.7 (1.7) | 1.0000 | 1.0000 |
| Fasting Insulin (mUI/L) | 12.1 (12.5) | 7.4 (6.2) | 1.0000 | 0.6799 |
| HOMA-R | 3.0 (3.5) | 2.0 (1.6) | 1.0000 | 0.8698 |
| Bone Turnover Markers | | | | |
| Osteocalcin (ng/mL) | 8.3 (3.8) | 3.0 (2.8)* | 0.3110 | 1.0000 |
| NTX (nMBCE/mM) | 37.2 (23.1) | −0.5 (27.7) | 1.0000 | 1.0000 |
| Immunologic Parameters | | | | |
| CD4 (cells/mm$^3$) | 577.0 (327.20) | −23.2 (70.7) | Contrasts ND (overall p = 0.3242) | overall p = 0.1259 |
| Viral load | No stats available due to undetectable values | | | |

[1]For GH and lipid parameters, the p-values presented are obtained from last observation data.
Results are mean (SD) in SI units Quality of Life A health-related quality of life questionnaire (PLC, Quality of Life Profile for the Chronically Ill) was self-administered to 61 patients randomized to receive placebo or TH9507 at 1 or 2 mg s.c. daily. The PLC questionnaire included a general, non-specific part assessing 6 dimensions of global health as well as a disease specific part capturing impact of enlarged abdominal girth, abdominal bloating, tenseness and pain, as well as diarrhea, visible facial changes, visible changes in physical appearance, and the feeling of being recognized as an HIV positive person.

Study population included 54 men and 7 women. Baseline mean age was 46±7 [SD], BMI 28±3 [SD] kg/m$^2$, WC 102 cm±8 [SD] and WHR 1.0±0.1 [SD]. No significant difference between groups was noted for subscales of the main portion of the PLC. Slight changes were observed within the treated groups in the positive mood and social well-being scores but were not considered clinically significant. Clinically significant improvements were noted in the enlarged abdominal girth (placebo: −0.13; 1 mg: −0.93, P=0.06 vs baseline; 2 mg: −1.19, P<0.05 vs baseline, NS vs placebo) and bloating scores (placebo: 0.56; 1 mg: −0.50; 2 mg: −0.69, P<0.05 vs. placebo). Improvement in abdominal pain was observed at 1 mg only (P<0.05 vs baseline, NS vs placebo) along with a trend for improvement in tenseness (P=0.07 vs baseline, NS vs placebo). No significant changes were observed in the other disease-specific items.

These data suggest that administration of TH9507, a GRF analog, in HIV patients with abdominal fat accumulation improved QOL with regard to enlarged abdominal girth and related items, consistent with the decrease in truncal and visceral fat observed in this population.

AE's and Discontinuation

Discontinuation rates were not different between the groups (24%, 11%, 29%, placebo, 1 mg, 2 mg respectively). One subject in the placebo group (arthritis), none in the 1 mg group and 3 in the 2 mg group (rash, arhtralgia, paresthesia) experienced AE's leading to treatment discontinuation. Severe AE's were reported in 6% of the placebo group, 13% of the 1 mg group and 10% of the 2 mg group. Musculoskeletal AE's e.g. pain and arthralgias were noted in 24%, 26% and 29% of subjects in the placebo, 1 mg and 2 mg groups respectively. Carpal tunnel symptoms were not noted in any patient. Edema and/or peripheral swelling were noted in 1 patient in the 2 mg group only. Headache and/or paresthesias were noted in 19%, 32% and 52% of the subjects in the placebo, 1 mg and 2 mg groups, respectively. Blood pressure and heart rate did not change between or within the groups. One patient in the placebo group compared to three in the 2 mg group withdrew from the study related to adverse events. Safety laboratory values, including hemoglobin, WBC, LFT's, creatinine did not differ between the groups (data not shown). CPK increased in a greater percentage of the 1 (47%) and 2 mg treated subjects (38%) compared to placebo (19%), but these changes were small and did not result in a greater proportion of abnormal CPK values between the groups. Anti-TH9507 antibodies were not detected after 12 weeks in any patient. CD4 count and viral load did not change.

Some of the results using a GRF analog in this study are comparable to that seen in response to GHRH 1-29 in a recently published study in men with HIV lipodystrophy, in which truncal fat, but not extremity or subcutaneous fat decreased in response to physiologic increases in GH (13). The current study extends the findings of Koutkia et al in a larger group of patients, including men and women, using graded doses of a novel 1-44 amino acid GRF analog that is dosed once rather than twice a day. Although the lower of the 2 doses increased IGF-I significantly, this dose did not result in a significant decrease in trunk fat, suggesting that there may be a threshold increase in IGF-I necessary to reduce truncal fat. Visceral fat also decreased significantly by more than 15% over 3 months within the 2 mg group. Of note, the magnitude of this change on a percentage basis is equivalent to that seen with pharmacologic doses of GH (9), suggesting that this strategy is highly effective and potentially very useful because of the general lack of side effects associated with physiologic increases in GH.

In addition to reducing truncal fat, the 2 mg GRF dose significantly improved triglyceride levels and the cholesterol to HDL ratio. This is a significant advantage of a GRF analog, not seen with other treatment strategies for HIV lipodystrophy (17, 18). Similar beneficial effects on triglyceride were seen with lower, alternating day, but not higher doses of GH in a study reported by Kotler et al. Growth hormone has been shown to decrease cholesterol and triglyceride levels in GH deficient patients and among otherwise healthy men chosen for abdominal obesity (19, 20). Taken together, our data suggest that treatment with TH9507 resulted in an improved lipid profile in dyslipidemic, abdominally obese patients with HIV lipodystrophy.

An important issue regarding the use of GH or related strategies in HIV lipodystrophy is glucose control. Patients with HIV lipodystrophy are often insulin resistant, and a significant percentage, more than a third, may have impaired glucose tolerance (3). In this study, even with the higher dose of 2 mg, there were no significant differences in fasting glucose or 2-hour glucose in response to a standard GTT and no increase in HbAIc.

TH9507 was also associated with other benefits in this study. Osteocalcin, a marker of bone formation increased within the 2 mg group, whereas NTX, a marker of bone resorption did not suggesting a net positive effect on bone turnover. Reduced bone density has been described among patients with HIV disease and among those with lipodystrophy, in inverse association with visceral and truncal adiposity (25, 26). Growth hormone is well known to stimulate bone formation (27). Relative reductions in GH secretion may therefore contribute to reduced bone density in some patients with lipodystrophy and a positive effect on bone formation, with physiologic increases in GH is an additional benefit of TH9507.

While the invention has been described in connection with specific embodiments thereof, it will be understood that it is capable of further modifications and this application is intended to cover any variations, uses, or adaptations of the invention following, in general, the principals of the invention and including such departures from the present disclosure as come within known or customary practice within the art to which the invention pertains and as may be applied to the essential features hereinbefore set forth, and as follows in the scope of the appended claims.

REFERENCES

1. Miller K D, Jones E, Yanovski J A, Shankar R, Feuerstein I, Falloon J. Visceral abdominal-fat accumulation associated with use of indinavir. Lancet 1998; 351(9106):871-5.
2. Carr A, Samaras K, Burton S, et al. A syndrome of peripheral lipodystrophy, hyperlipidaemia and insulin resistance in patients receiving HIV protease inhibitors. AIDS 1998; 12(7):F51-8.
3. Hadigan C, Meigs J B, Corcoran C, et al. Metabolic Abnormalities and Cardiovascular Disease Risk Factors in Adults with Human Immunodeficiency Virus Infection and Lipodystrophy. Clin Infect Dis 2001; 32(1):130-9.
4. Friis-Moller N, Sabin C A, Weber R, et al. Combination antiretroviral therapy and the risk of myocardial infarction. N Engl J Med 2003; 349(21):1993-2003.
5. Pouliot M C, Despres J P, Nadeau A. Visceral Obesity in Men: Associations with Glucose Tolerance, Plasma Insulin and Lipoprotein Levels. Diabetes 1992; 41:826-34.
6. Meininger G, Hadigan C, Rietschel P, Grinspoon S. Body-composition measurements as predictors of glucose and insulin abnormalities in HIV-positive men. Am J Clin Nutr 2002; 76(2):460-5.
7. Rietschel P, Hadigan C, Corcoran C, et al. Assessment of Growth Hormone Dynamics in Human Immunodeficiency Virus-Related Lipodystrophy. J Clin Endocrinol Metab 2001; 86(2):504-10.
8. Koutkia P, Meininger G, Canavan B, Breu J, Grinspoon S. Metabolic regulation of growth hormone by free fatty acids, somatostatin, and ghrelin in HIV-lipodystrophy. Am J Physiol Endocrinol Metab 2004; 286(2):E296-303.
9. Kotler D P, Muurahainen N, Grunfeld C, et al. Effects of growth hormone on abnormal visceral adipose tissue accumulation and dyslipidemia in HIV-infected patients. J Acquir Immune Def Syndr 2004; 35:239-52.
10. Engelson E S, Glesby M J, Mendez D, et al. Effect of recombinant human growth hormone in the treatment of visceral fat accumulation in HIV infection. J Acquir Immune Defic Syndr 2002; 30(4):379-91.
11. Wanke C, Gerrior J, Kantaros J, Coakley E, Albrecht M. Recombinant human growth hormone improves the fat redistribution syndrome (lipodystrophy) in patients with HIV. AIDS 1999; 13(15):2099-103.
12. Lo J C, Mulligan K, Noor M A, et al. The effects of recombinant human growth hormone on body composition and glucose metabolism in HIV-infected patients with fat accumulation. J Clin Endocrinol Metab 2001; 86(8):3480-7.
13. Koutkia P, Canavan B, Breu J, Toriani M, Kissko J, Grinspoon S. Growth Hormone-releasing Hormone in HIV-infected Men with Lipodystrophy: A Randomized, Controlled Trial. JAMA 2004; 292:210-8.
14. Abribat T, Gravel D, Brazeau P. TH9507 A new Growth Hormone-Releasing Factor (GRF) analogue is a powerful Insulin-like Growth Factor-1 (IGF-1) inducer in 50-60 years old healthy subjects: A 7-Day, Randomizeed Multi-dose Study. In: The Endocrine Society's 84 rd Annual Meeting; 2001; Denver; 2001. p. P2-292.
15. Clemmons D, Miller S, De Villers A, et al. Safety assessment and metabolic effects of TH9507, a Growth Hormone Releasing Factor analog (GRF) in patients with Type 2 diabetes mellitus. In: The Endocrine Society's 86 Annual Meeting; 2003; Philadelphia; 2003. p. P2-354.
16. Park Y W, Heymsfield S B, Gallagher D. Are dual-energy X-ray absorptiometry regional estimates associated with visceral adipose tissue mass? International Journal of Obesity & Related Metabolic Disorders: Journal of the International Association for the Study of Obesity 2002; 26(7): 978-83.
17. Hadigan C, Yawetz S, Thomas A, Havers F, Sax P E, Grinspoon S. Metabolic effects of rosiglitazone in HIV lipodystrophy: A randomized controlled trial. Annals of Internal Medicine 2004; 140(10):786-94.
18. Hadigan C, Corcoran C, Basgoz N, Davis B, Sax P, Grinspoon S. Metformin in the treatment of HIV lipodystrophy syndrome: A randomized controlled trial. JAMA 2000; 284(4):472-7.
19. Johannsson G, Marin P, Lonn L, et al. Growth hormone treatment of abdominally obese men reduces abdominal fat mass, improves glucose and lipoprotein metabolism, and reduces diastolic blood pressure. J Clin Endocrinol Metab 1997; 82(3):727-34.
20. Colao A, di Somma C, Cuocolo A, et al. Improved cardiovascular risk factors and cardiac performance after 12 months of growth hormone (GH) replacement in young adult patients with GH deficiency. J Clin Endocrinol Metab 2001; 86(5):1874-81.

What is claimed is:

1. A method of improving cognitive function in a subject suffering from mild cognitive impairment, said method comprising administering to said subject:

(a) (hexenoyl trans-3)hGRF(1-44)NH$_2$; or
   (b) a composition comprising (hexenoyl trans-3)hGRF(1-44)NH$_2$ and a pharmaceutically acceptable carrier.

2. The method of claim 1, wherein said cognitive function is thinking, reasoning, problem solving or memory.

3. The method of claim 1, wherein said (hexenoyl trans-3)hGRF(1-44)NH$_2$ is administered at a dose of about 0.0001 to 2 mg.

4. The method of claim 3, wherein said (hexenoyl trans-3)hGRF(1-44)NH$_2$ is administered at a dose of about 0.1 mg or about 1 mg.

5. The method of claim 4, wherein said (hexenoyl trans-3)hGRF(1-44)NH$_2$ is administered at a dose of about 1 mg.

6. The method of claim 1, wherein said (hexenoyl trans-3)hGRF(1-44)NH$_2$ or said composition is administered by an intravenous, oral, transdermal, subcutaneous, mucosal, intramuscular, intranasal, intrapulmonary, parenteral, intrarectal or topical route.

7. The method of claim 6, wherein said (hexenoyl trans-3)hGRF(1-44)NH$_2$ or said composition is administered by a subcutaneous route.

* * * * *

SEQUENCE LISTING

```
<160> NUMBER OF SEQ ID NOS: 7

<210> SEQ ID NO 1
<211> LENGTH: 44
<212> TYPE: PRT
<213> ORGANISM: Artificial sequence
<220> FEATURE:
<223> OTHER INFORMATION: Synthetic GRF peptide
<220> FEATURE:
<221> NAME/KEY: VARIANT
<222> LOCATION: (1)..(1)
<223> OTHER INFORMATION: Xaa = Tyr or His
<220> FEATURE:
<221> NAME/KEY: VARIANT
<222> LOCATION: (2)..(2)
<223> OTHER INFORMATION: Xaa = Val or Ala
<220> FEATURE:
<221> NAME/KEY: VARIANT
<222> LOCATION: (8)..(8)
<223> OTHER INFORMATION: Xaa = Asn or Ser
<220> FEATURE:
<221> NAME/KEY: VARIANT
<222> LOCATION: (13)..(13)
<223> OTHER INFORMATION: Xaa = Val or Ile
<220> FEATURE:
<221> NAME/KEY: VARIANT
<222> LOCATION: (15)..(15)
<223> OTHER INFORMATION: Xaa = Ala or Gly
<220> FEATURE:
<221> NAME/KEY: VARIANT
<222> LOCATION: (18)..(18)
<223> OTHER INFORMATION: Xaa = Ser or Tyr
<220> FEATURE:
<221> NAME/KEY: VARIANT
<222> LOCATION: (24)..(24)
<223> OTHER INFORMATION: Xaa = Gln or His
<220> FEATURE:
<221> NAME/KEY: VARIANT
<222> LOCATION: (25)..(25)
<223> OTHER INFORMATION: Xaa = Asp or Glu
<220> FEATURE:
<221> NAME/KEY: VARIANT
<222> LOCATION: (27)..(27)
<223> OTHER INFORMATION: Xaa = Met or Ile or Nle
<220> FEATURE:
<221> NAME/KEY: VARIANT
<222> LOCATION: (28)..(28)
<223> OTHER INFORMATION: Xaa = Ser or Asn
<220> FEATURE:
<221> NAME/KEY: VARIANT
<222> LOCATION: (30)..(30)
<223> OTHER INFORMATION: Xaa = any amino acid or is absent
<220> FEATURE:
<221> NAME/KEY: VARIANT
<222> LOCATION: (31)..(31)
<223> OTHER INFORMATION: Xaa = any amino acid or is absent
<220> FEATURE:
<221> NAME/KEY: VARIANT
<222> LOCATION: (32)..(32)
<223> OTHER INFORMATION: Xaa = any amino acid or is absent
<220> FEATURE:
<221> NAME/KEY: VARIANT
<222> LOCATION: (33)..(33)
```

```
<223> OTHER INFORMATION: Xaa = any amino acid or is absent
<220> FEATURE:
<221> NAME/KEY: VARIANT
<222> LOCATION: (34)..(34)
<223> OTHER INFORMATION: Xaa = any amino acid or is absent
<220> FEATURE:
<221> NAME/KEY: VARIANT
<222> LOCATION: (35)..(35)
<223> OTHER INFORMATION: Xaa = any amino acid or is absent
<220> FEATURE:
<221> NAME/KEY: VARIANT
<222> LOCATION: (36)..(36)
<223> OTHER INFORMATION: Xaa = any amino acid or is absent
<220> FEATURE:
<221> NAME/KEY: VARIANT
<222> LOCATION: (37)..(37)
<223> OTHER INFORMATION: Xaa = any amino acid or is absent
<220> FEATURE:
<221> NAME/KEY: VARIANT
<222> LOCATION: (38)..(38)
<223> OTHER INFORMATION: Xaa = any amino acid or is absent
<220> FEATURE:
<221> NAME/KEY: VARIANT
<222> LOCATION: (39)..(39)
<223> OTHER INFORMATION: Xaa = any amino acid or is absent
<220> FEATURE:
<221> NAME/KEY: VARIANT
<222> LOCATION: (40)..(40)
<223> OTHER INFORMATION: Xaa = any amino acid or is absent
<220> FEATURE:
<221> NAME/KEY: VARIANT
<222> LOCATION: (41)..(41)
<223> OTHER INFORMATION: Xaa = any amino acid or is absent
<220> FEATURE:
<221> NAME/KEY: VARIANT
<222> LOCATION: (42)..(42)
<223> OTHER INFORMATION: Xaa = any amino acid or is absent
<220> FEATURE:
<221> NAME/KEY: VARIANT
<222> LOCATION: (43)..(43)
<223> OTHER INFORMATION: Xaa = any amino acid or is absent
<220> FEATURE:
<221> NAME/KEY: VARIANT
<222> LOCATION: (44)..(44)
<223> OTHER INFORMATION: Xaa = any amino acid or is absent
<220> FEATURE:
<221> NAME/KEY: MOD_RES
<222> LOCATION: (44)..(44)
<223> OTHER INFORMATION: C-terminal residue is modified with NH2 or
      NH-(CH2)n-CONH2, with n=1 to 12

<400> SEQUENCE: 1

Xaa Xaa Asp Ala Ile Phe Tyr Xaa Ser Tyr Arg Lys Xaa Leu Xaa Gln
1               5                   10                  15

Leu Xaa Ala Arg Lys Leu Leu Xaa Ile Xaa Xaa Arg Xaa Xaa Xaa
            20                  25                  30

Xaa Xaa Xaa Xaa Xaa Xaa Xaa Xaa Xaa Xaa Xaa Xaa
        35                  40

<210> SEQ ID NO 2
<211> LENGTH: 44
<212> TYPE: PRT
<213> ORGANISM: Homo sapiens
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 2

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30
```

```
Glu Ser Asn Gln Glu Arg Gly Ala Arg Ala Arg Leu
        35                  40

<210> SEQ ID NO 3
<211> LENGTH: 44
<212> TYPE: PRT
<213> ORGANISM: Artificial sequence
<220> FEATURE:
<223> OTHER INFORMATION: Amino acid sequence of human GRF

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 4
<211> LENGTH: 29
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Arg residue is capped with an unsubstituted
      amide moiety

<400> SEQUENCE: 4

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 5
<211> LENGTH: 29
<212> TYPE: PRT
<213> ORGANISM: Artificial sequence
<220> FEATURE:
<223> OTHER INFORMATION: Amino acid sequence of the minimum active core
      of human GRF

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 6
<211> LENGTH: 15
<212> TYPE: PRT
<213> ORGANISM: Artificial sequence
<220> FEATURE:
<223> OTHER INFORMATION: Amino acid sequence corresponding to positions
      30 to 44 of human GRF

<400> SEQUENCE: 6

Gln Gln Gly Glu Ser Asn Gln Glu Arg Gly Ala Arg Ala Arg Leu
1               5                   10                  15

<210> SEQ ID NO 7
<211> LENGTH: 44
<212> TYPE: PRT
<213> ORGANISM: Artificial sequence
<220> FEATURE:
<223> OTHER INFORMATION: Synthetic modified GRF peptide
```

```
-continued

<220> FEATURE:
<221> NAME/KEY: MISC_FEATURE
<222> LOCATION: (1)..(1)
<223> OTHER INFORMATION: Tyr residue is linked to an hexenoyl-trans-3
      moiety
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 7

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40
```